United States Patent
Sone et al.

(10) Patent No.: US 6,719,976 B1
(45) Date of Patent: Apr. 13, 2004

(54) PEPTIDE-BASED IMMUNOTHERAPEUTIC AGENT FOR TREATING ALLERGIC DISEASES

(75) Inventors: Toshio Sone, Kanagawa (JP); Akinori Kume, Kanagawa (JP); Kazuo Dairiki, Kanagawa (JP); Akiko Iwama, Kanagawa (JP); Kohsuke Kino, Kanagawa (JP)

(73) Assignee: Meiji Milk Products Co., Ltd. (JP)

( * ) Notice: Subject to any disclaimer, the term of this patent is extended or adjusted under 35 U.S.C. 154(b) by 0 days.

(21) Appl. No.: 09/142,524

(22) PCT Filed: Mar. 10, 1997

(86) PCT No.: PCT/JP97/00740

§ 371 (c)(1),
(2), (4) Date: Jan. 4, 1999

(87) PCT Pub. No.: WO97/32600

PCT Pub. Date: Sep. 12, 1997

(30) Foreign Application Priority Data

Mar. 10, 1996 (JP) ............................... 8-080702

(51) Int. Cl.⁷ .................. A61K 38/00; A61K 39/00; A61K 39/35; A61K 39/36
(52) U.S. Cl. ............. 424/192.1; 424/193.1; 424/194.1; 424/275.1; 514/12; 530/324
(58) Field of Search .......... 424/192.1, 193.1, 424/194.1, 275.1; 514/12, 885; 530/324

(56) References Cited

FOREIGN PATENT DOCUMENTS

| JP | 08047392 A | * | 2/1996 | |
|---|---|---|---|---|
| WO | WO 93/08280 A1 | | 4/1993 | |
| WO | 9401560 | | 1/1994 | |
| WO | WO/94/01560 | * | 1/1994 | ........... C12N/15/29 |
| WO | WO 94/11512 | * | 5/1994 | |

OTHER PUBLICATIONS

Peptide Chemistry, vol. 33, pp. 409–412, 1996.*
Rogers et al. Molecular Immunology, vol. 31, No. 13, pp 955–966, 1994.*
Suzuki, M. et al., "Purification, Characterization and Molecular Cloning of Cha o 1, A Major Allergen of *Chamaecyparis Obtusa* (Japanese Cypress) Pollen", *Mol. Immunol.* (1996), 33:4/5:451–460; Elsevier Science Ltd., Great Britain.
Taniai, Madoka, Shunsaku, Ando, Mitsuko Usui, Masashi Kurimoto et al. (Nov. 1988) "N–terminal amino acid sequence of a major allergen of Japanese ceder pollen (Cry j 1)" 60 *FEBS LETTERS 239(2):329–332*.
Rogers, Bruce L., Julian F. Bond, Sandra J. Craig et al. (1994) "Potential Therapeutic Recombinant Proteins Comprised Of Peptides Containing Recombined T Cell Epitopes" *Molecular Immunology* 31(13):955–966.
Komiyama, Naoki, Toshio Sone, Kimiko Shimizu, Keiko Morikubo, Hohsuke Kino (Jun. 15, 1994) "cDNA Cloning And Expression of Cry j II, the Second Major Allergen of Japanese Cedar Pollen" *Biochemical and Biophysical Research Communications* 201(2):1021–1028.
Higgins, Julie A., Christopher J. Thorpe, John D. Hayball, Robyn E. O'Hehir, Jonathan R. Lamb (May 1994) "Overlapping T–cell epitopes in the group I allergen of *Dermatophagoides species* restricted by HLA–DP and HLA–DR class II molecules" *J. Allergy Clin. immunol.* pp. 891–899.
Matsunaga, Youchi, Toshiji Saibara, Hiroshi Kido, Nobuhiko Katunuma (Jun. 1993) "Participation of cathepsin B in processing of antigen presentation to MHC class II" *FEBS LETTTERS* 324(3):325–330.
LaSalle, Janine M., Paul J. Tolentino, Gordon J. Freeman, Lee M. Nadler, David A. Hafler (Jul. 1992) "Early Signaling Defects in Human T Cells Anergized by T Cell Presentation of Autoantigen"*J. Exp. Med.* 176:177–186.
Simons, F. Estelle R., Mie Imada, Yan Li, Wade T.A. Watson, Kent T. HayGlass (1996) "Fel d 1 peptides: effect on skin tests and cytokine synthesis in cat–allergic human subjects" *International Immunology* 8(12):1937–1945.
Brinker, Thomas J., Mei–Chang Kuo, Kathleen M. Keating, Bruce L. Rogers, Julie L. Greenstein (Aug. 1993) "Peripheral T–cell tolerance induced in naive and primed mice by subcutaneous injection of peptides from the major cat allergen Fel d I" *Proc. Natl. Acad. Sci. USA* 90:7608–7612.
Sakaguchi, M., S. Inouye, M. Taniai, S. Ando, M. Usui, T. Matuhasi (1990) "Identification of the second major allergen of Japanese cedar pollen" *Allergy* 45:309–312.
Norman, Philip S., John L. Ohman, Jr., A.A. Long, Peter S. Creticos et al. (1996) "Treatment of Cat Allergy with T–cell Reactive Peptides" *Am J Respir Crit Care Med* 154:1623–1628.
Wallner, B.P., M.L. Gefter (1994) "Immunotherapy with T–cell–reactive peptides derived from allergens" *Allergy* 49:302–308.
Yasueda, Hiroshi, Yasuo Yui, Takaharu Shimizu, Takao Shida (1983) "Isolation and partial characterization of the major allergen from Japanese cedar (*Cryptomeria japonica*) pollen" *J. Allergy Clin. Immunol.* 71(1) part 1:77–86.
Hashimoto, M., H. Nigi, M. Sakaguchi, S. Inouye et al. (1995) "Sensitivity to two major allergens ( Cry j I and Cry j II) in patients with Japanese cedar (*Cryptomeria japonica*) pollinosis" *Clinical and Experimetnal Allergy* 25:848–852.
Rammensee, Hans–Georg, Thomas Friede, Stefan Stevanovic (1995) "MHC ligands and peptide motifs: first listing" *Immunogenetics* 41:178–228.

* cited by examiner

Primary Examiner—Christina Y. Chan
Assistant Examiner—Marianne DiBrino
(74) *Attorney, Agent, or Firm*—Saliwanchik, Lloyd & Saliwanchik

(57) ABSTRACT

The present invention provides a monomolecular multi-epitope peptide prepared by binding T cell epitope regions derived from different allergen molecules with each other. A peptide-based immunotherapeutic agent containing an effective amount of the multi-epitope peptide can treat a wide range of allergic diseases.

11 Claims, 19 Drawing Sheets

Th TYPE OF T CELL CLONE CAPABLE OF RECOGNIZING Cry j 1

| T CELL CLONE | EPITOPE SITE NO. | POSITION | RESTRICTION MOLECULE | LYMPHOKINE PRODUCTION (pg/ml) | | | Th* TYPE |
|---|---|---|---|---|---|---|---|
| | | | | IL-2 | IFNγ | IL-4 | |
| PJ4-6 | 4 | 16- 30 | DQA1*0102 DQB1*0602 | <31 | 1500 | 334 | Th0 |
| PB8-1 | 4 | 16- 30 | " | <31 | <31 | 814 | Th2 |
| PB9-37 | 13 | 61- 75 | DPA1*0101-DPB1*0501 | <31 | <31 | 7760 | Th2 |
| PB10-24 | 13 | 61- 75 | " | 39 | 151 | 4500 | Th2 |
| PJ1-27 | 19 | 91-105 | DQ | 32 | 1220 | 224 | Th0 |
| PB3-27 | 22 | 106-120 | DRB5*0101 | 250 | 332 | 21000 | Th2 |
| PB8-2 | 22 | 106-120 | " | 190 | 2110 | 5709 | Th0 |
| PB8-3 | 22 | 106-120 | " | <31 | 1270 | 10100 | Th0 |
| PB9-39 | 22 | 106-120 | " | 48 | 51 | 5120 | Th2 |
| PB10-18 | 22 | 106-120 | " | 410 | 46 | 7840 | Th2 |
| PJ4-29 | 22 | 106-120 | " | 4680 | 14200 | 6610 | Th0 |
| PJ7-9 | 22 | 106-120 | " | 1370 | 1040 | 12200 | Th2 |
| PJ5-6 | 30 | 145-160 | DQA1*0102-DQB1*0602 | 1500 | 1170 | 5920 | Th0 |
| PJ5-9 | 30 | 145-160 | " | 1720 | 825 | 266 | Th0 |
| PB11-21 | 31 | 151-165 | DRB1*0901 | 4190 | >20000 | 4510 | Th0 |
| PB11-24 | 31 | 151-165 | " | 670 | 11700 | 1950 | Th0 |
| PB6-37 | 31 | 151-165 | " | <31 | <31 | 49 | Th2 |
| PB1-8 | 39 | 191-205 | DQA1*0102-DQB1*0602 | 820 | 188 | 1760 | Th0 |
| PB9-34 | 39 | 191-205 | DRB1*0901 OR DRB4*0101 | <31 | 86 | 1680 | Th2 |
| PB2-14 | 43 | 211-225 | DPA1*0101-DPB1*0501 | <31 | 376 | 2320 | Th0 |
| PB7-2 | 43 | 211-225 | " | 84 | 2740 | 2080 | Th0 |
| PB8-32 | 43 | 211-225 | " | <31 | 4870 | 1840 | Th0 |
| PB8-34 | 43 | 211-225 | " | 78 | 14800 | 3040 | Th0 |
| PB11-23 | 43 | 211-225 | " | <31 | 3990 | 1260 | Th0 |
| PB11-26 | 43 | 211-225 | " | 32 | 1100 | 6520 | Th0 |
| PB4-20 | 43 | 211-225 | " | <31 | <31 | 133 | Th2 |
| PB10-4 | 43 | 211-225 | " | <31 | <31 | 4170 | Th2 |
| PB8-4 | 51 | 251-265 | DQA1*0102-DQB1*0602 | 44 | 36 | 4050 | Th2 |
| PJ4-20 | 66 | 326-340 | DQA1*0102-DQB1*0602 | 560 | 3080 | <32 | Th1 |

* IL-4/IFN-γ > 10 AND IFN-γ/IL-4 > 10 ARE DEFINED TO BE Th2 AND Th1, RESPECTIVELY, AND Th0 MEANS INBETWEEN.

FIG. 3

Th TYPE OF T CELL CLONE CAPABLE OF RECOGNIZING Cry j 2

| T CELL CLONE | EPITOPE SITE NO. | POSITION | RESTRICTION MOLECULE | LYMPHOKINE PRODUCTION (pg/ml) | | | Th* TYPE |
|---|---|---|---|---|---|---|---|
| | | | | IL-2 | IFNγ | IL-4 | |
| PB5-29 | 4 | 16- 30 | DRB1*0901 OR DRB4*0101 | <31 | 503 | 97 | Th0 |
| PB11-40 | 4 | 16- 30 | " | <31 | <31 | 50 | Th2 |
| PB14-4 | 4 | 16- 30 | " | <31 | <31 | <16 | Thp |
| PB12-33 | 8 | 36- 50 | DRB1*1501 | <31 | >8000 | <16 | Th1 |
| PR2-25 | 8 | 36- 50 | " | 47 | <31 | 977 | Th2 |
| PR5-40 | 8 | 36- 50 | " | 1150 | 1330 | 355 | Th0 |
| PB3-32 | 14 | 66- 80 | DRB5*0101 | <31 | <31 | 323 | Th2 |
| PB4-21 | 14 | 66- 80 | " | <31 | 109 | 239 | Th0 |
| PB4-22 | 14 | 66- 80 | " | <31 | 483 | 158 | Th0 |
| PC1-8 | 14 | 66- 80 | " | <31 | 2710 | 32 | Th1 |
| PR4-20 | 14 | 66- 80 | " | <31 | 312 | 338 | Th0 |
| PR3-21 | 14 | 66- 80 | " | <31 | <31 | 338 | Th2 |
| PB13-18 | 17 | 76- 90 | DPA1*0101-DPB1*0501 | <31 | 3320 | 231 | Th1 |
| PB11-32 | 17 | 76- 90 | " | 138 | 60 | 2090 | Th2 |
| PR1-20 | 31 | 151-165 | DRB1*0901 | <31 | <31 | 18 | Th2 |
| PR4-39 | 31 | 151-165 | " | <31 | <31 | <16 | Thp |
| PB14-5 | 37 | 181-195 | DPA1*0101-DPB1*0201 | 87 | 126 | 469 | Th0 |
| PB14-13 | 37 | 181-195 | " | <31 | 59 | 2440 | Th2 |
| PB14-34 | 38 | 186-200 | DRB4*0101 | 186 | 420 | 93 | Th0 |
| PC3-40 | 38 | 186-200 | " | <31 | <31 | 379 | Th2 |
| PB5-3 | 48 | 236-250 | DRB1*1501 OR DRB5*0101 | 2570 | >8000 | 525 | Th1 |
| PR2-34 | 65 | 321-335 | DRB1*0901 | 57 | 1990 | 464 | Th0 |
| PR3-30 | 66 | 326-340 | DQA1*0102-DQB1*0602 | <31 | 106 | <80 | Th1 |
| PR5-18 | 66 | 326-340 | " | <31 | <31 | <16 | Thp |
| PC1-13 | 68 | 336-350 | DPA1*0202-DPB1*0501 | <31 | <31 | <16 | Thp |
| PB12-8 | 69 | 341-355 | DQA1*0102-DQB1*0602 | <31 | 3210 | <16 | Th1 |
| PR5-12 | 69 | 341-355 | " | <31 | <31 | 2528 | Th2 |
| PR2-31 | 69 | 341-355 | " | <31 | <31 | 332 | Th2 |
| PB14-19 | 70 | 346-360 | " | <31 | 3730 | <16 | Th1 |
| PB13-38 | 70 | 346-360 | " | <31 | 2020 | <16 | Th1 |

* IL-4/IFN-γ > 10 AND IFN-γ/IL-4 > 10 ARE DEFINED TO BE Th2 AND Th1, RESPECTIVELY, Th0 MEANS INBETWEEN, AND Thp MEANS NOT SHOWING THE PRODUCTION OF LYMPHOKINE.

FIG. 4

| | |
|---|---|
| a | Lys Ser Met Lys Val Thr Val Ala Phe Asn Gln Phe Gly Pro Asn |
| b | Pro Cys Val Phe Ile Lys Arg Val Ser Asn Val Ile Ile His Gly |
| c | Val Asp Gly Ile Ile Ala Ala Tyr Gln Asn Pro Ala Ser Trp Lys |
| d | Gly Ile Asp Ile Phe Ala Ser Lys Asn Phe His Leu Gln Lys Asn Thr Ile Gly Thr Gly |
| e | Leu Lys Leu Thr Ser Gly Lys Ile Ala Ser Cys Leu Asn Asp Asn Ala Asn Gly Tyr Phe |

FIG. 7

REACTIVITY OF PEPTIDE COMPOSITIONS (#1 - #6) WITH HUMAN IgE

| SAMPLE NO. (SERA) | BLANK | CEDAR POLLEN-EXTRACTED ANTIGEN | C.A. #1 | C.A. #2 | C.A. #3 | C.A. #4 | C.A. #5 | C.A. #6 |
|---|---|---|---|---|---|---|---|---|
| 1 | 3 | 2105 | 5 | 4 | 3 | 4 | 4 | 4 |
| 2 | 3 | 1133 | 4 | 4 | 4 | 4 | 4 | 4 |
| 3 | 3 | 1126 | 3 | 3 | 3 | 4 | 4 | 3 |
| 4 | 3 | 1095 | 4 | 3 | 3 | 3 | 3 | 3 |
| 5 | 3 | 1047 | 3 | 3 | 3 | 3 | 3 | 3 |
| 6 | 3 | 1003 | 3 | 4 | 3 | 3 | 3 | 3 |
| 7 | 4 | 710 | 4 | 4 | 4 | 4 | 4 | 4 |
| 8 | 3 | 521 | 3 | 3 | 3 | 3 | 3 | 3 |
| 9 | 3 | 314 | 3 | 3 | 4 | 3 | 4 | 4 |
| 10 | 3 | 298 | 3 | 3 | 4 | 4 | 4 | 3 |
| 11 | 3 | 279 | 3 | 3 | 3 | 3 | 3 | 3 |
| 12 | 3 | 253 | 3 | 3 | 3 | 3 | 3 | 3 |
| 13 | 3 | 239 | 3 | 3 | 3 | 3 | 3 | 3 |
| 14 | 3 | 235 | 4 | 4 | 4 | 4 | 4 | 4 |
| 15 | 3 | 233 | 3 | 3 | 3 | 3 | 3 | 3 |
| 16 | 3 | 226 | 4 | 4 | 4 | 4 | 4 | 3 |
| 17 | 3 | 190 | 3 | 3 | 3 | 3 | 3 | 3 |
| 18 | 3 | 162 | 4 | 4 | 4 | 4 | 4 | 4 |
| 19 | 3 | 123 | 3 | 3 | 3 | 3 | 3 | 3 |
| 20 | 3 | 106 | 3 | 3 | 3 | 3 | 3 | 3 |
| 21 | 4 | 45 | 3 | 3 | 3 | 3 | 3 | 3 |
| 22 | 3 | 14 | 3 | 3 | 3 | 3 | 3 | 3 |
| 23 | 3 | 13 | 3 | 3 | 3 | 3 | 3 | 3 |
| 24 | 3 | 11 | 3 | 3 | 3 | 3 | 3 | 3 |
| 25 | 3 | 5 | 4 | 4 | 4 | 4 | 4 | 4 |
| 26 | 3 | 4 | 4 | 4 | 3 | 4 | 4 | 3 |
| 27 | 3 | 3 | 3 | 3 | 3 | 3 | 3 | 3 |
| 28 | 3 | 3 | 3 | 3 | 3 | 3 | 3 | 3 |
| 29 | 3 | 3 | 3 | 4 | 3 | 3 | 3 | 3 |
| RABBIT anti-PEPTIDE IgG | 112 | 230 | 3754 | 3829 | 3769 | 3716 | 3841 | 3798 |

FIG. 8

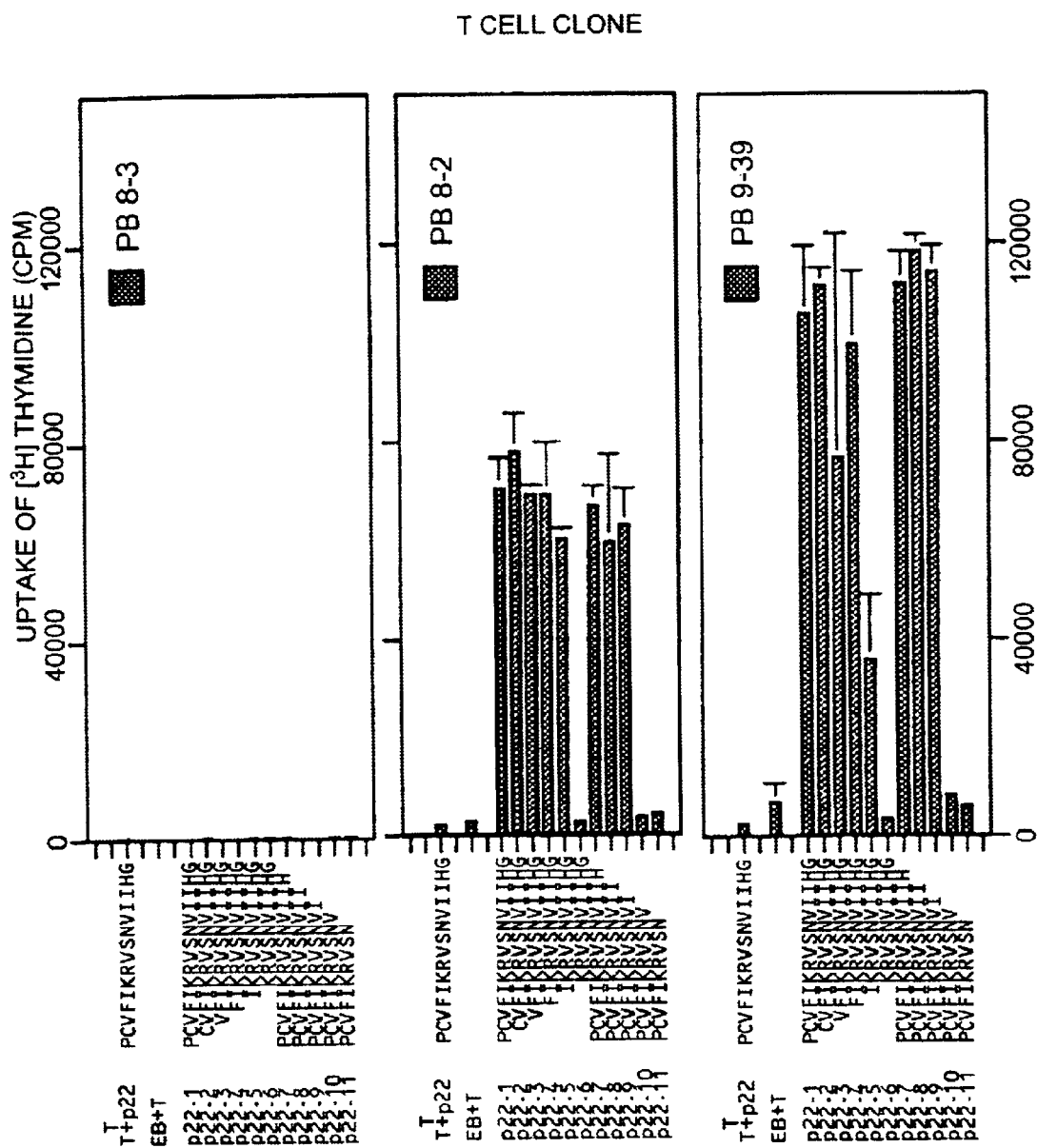
FIG. 15 (1)

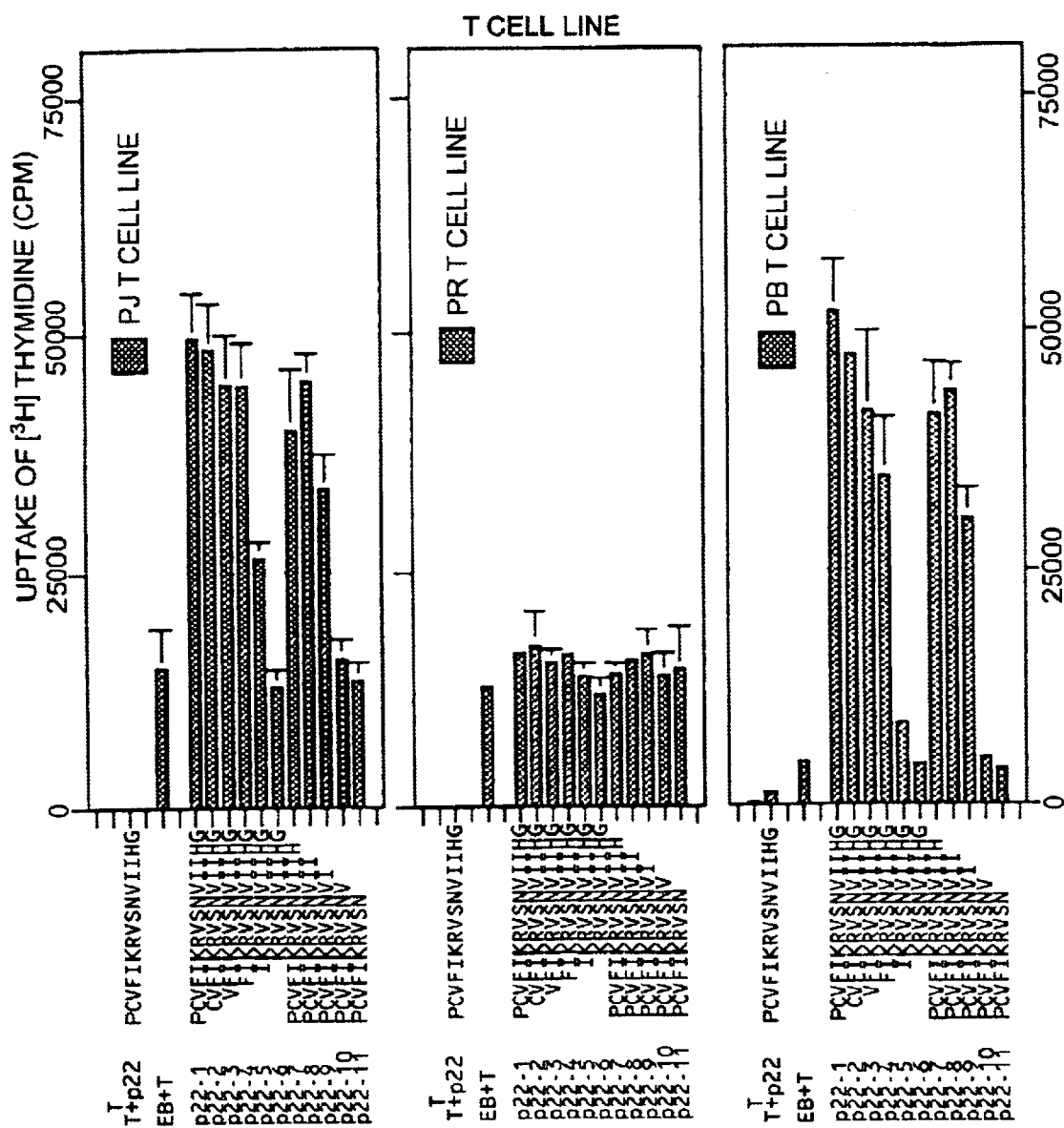
FIG. 15 (2)

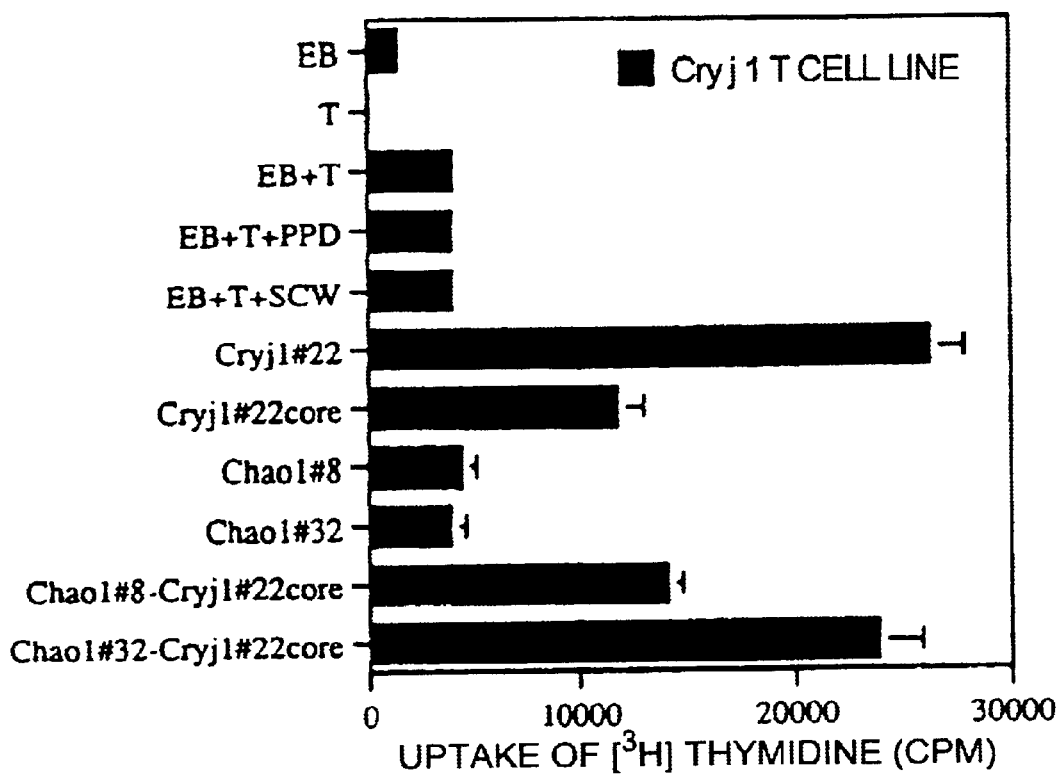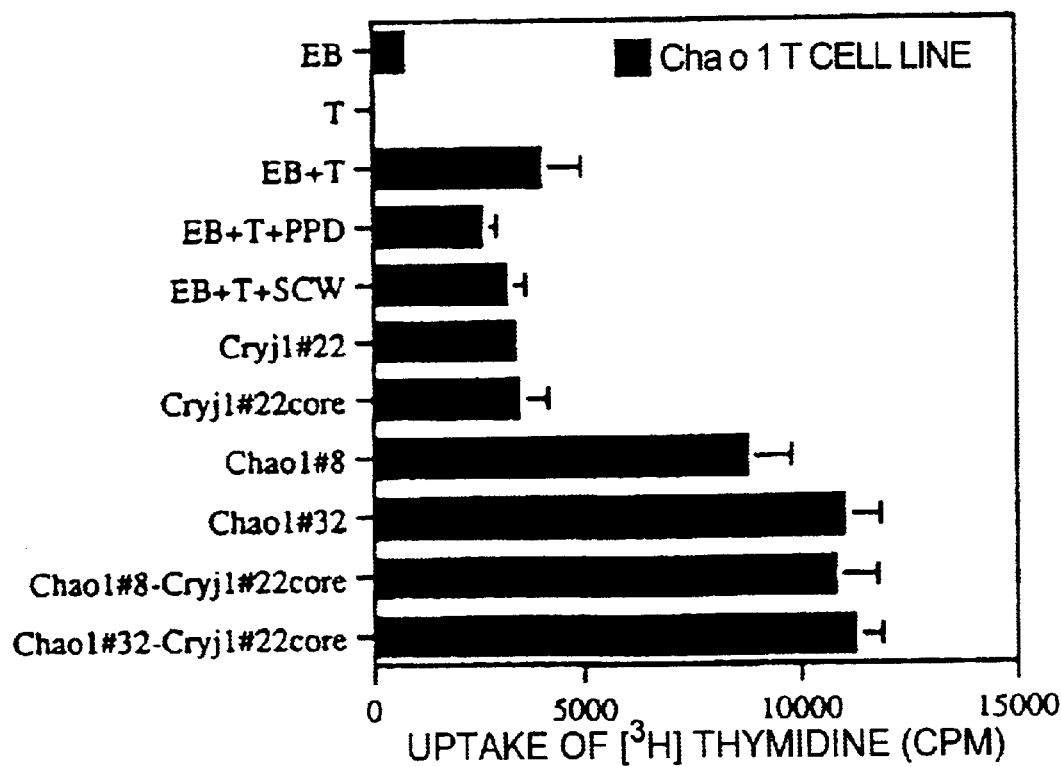
FIG. 16

PEPTIDE-BASED IMMUNOTHERAPEUTIC AGENT FOR TREATING ALLERGIC DISEASES

TECHNICAL FIELD

The present invention relates to a multi-epitope peptide, which is useful for peptide-based immunotherapy of allergic diseases.

BACKGROUND ART

Allergic diseases are defined to be functional disturbances caused by type I hypersensitivity (type I immune response mediated by IgE antibodies) or a kind of disease induced by the disturbance. The symptoms include pollinosis, bronchial asthma, allergic rhinitis, atopic dermatitis, and anaphylactic shock. Pollinosis is a representative allergic disease. In Japan, approximately 10% of the population suffers from cedar pollinosis, and the number of the patients is still increasing. In America, 5 to 15% of the population suffers from short ragweed pollinosis. Pollinosis is a serious problem both socially and economically because there are many patients and they suffer from unbearable conditions such as itchiness of eyes, runny noses, sneezing, and nasal congestion. Moreover, once the patient acquires pollinosis, the disease manifests itself every year. An effective therapy for pollinosis has thus earnestly been sought.

To comprehend and treat allergic diseases, it is important to understand how a type I allergic response is developed. Current studies focus on clarifying the initial reaction in the allergen-specific immune response, especially the mechanism of regulating a T cell-mediated allergic reaction. Initiation of an immune response to a foreign antigen including an allergen depends on antigen-presenting cells in the immune system. The antigen-presenting cells (i.e., B cells, macrophages, and dendritic cells) take up incoming foreign antigens, break them down to antigen peptides (T cell epitope peptides), put the fragments in a pocket consisting of α and β chains of major histocompatibility complex (MHC) class II molecules (HLA class II in human), display the fragments on the cell surface, and thereby present the foreign antigens to antigen-specific CD4 positive helper T cells (Th cells). An HLA class II molecule consists of DR, DQ and DP molecules. The α-chain of the DR molecule is encoded by the HLA-DRA gene, and the β-chain is encoded by the HLA-DRB1, -DRB3, -DRB4 or -DRB5 gene. The α-chain of the DQ molecule is encoded by the HLA-DQA1 gene, and the, βchain is encoded by the HLA-DQB1 gene. The α-chain of the DP molecule is encoded by the HLA-DPA1 gene, and the β-chain is encoded by the HLA-DPB1 gene. Each gene except for HLA-DRA contains many alleles. The pocket in which antigenic peptides are placed is highly polymorphic, and the structures differ slightly from each other. Because of this, the kind of antigenic peptides that bind to the pocket and are presented to T cells is restricted to that structure.

Once Th cells receive HLA class II-restricting antigen information via the T cell receptor (TCR), they are activated to secrete various cytokines, by which they proliferate by themselves. At the same time, the Th cells induce differentiation of B cells into plasma cells, to induce antibody production. Depending upon the difference in the cytokine-producing pattern, the Th cells activated by antigen stimulation are classified into Th 1 cells capable of producing interferon 2 (IL-2), interferonγ (IFN-γ) and lymphotoxin (TNF-β); Th 2 cells capable of producing IL-4, IL-5, IL-6, IL-10 and IL-13; and Th0 cells capable of producing both cytokines. The production of IgE antibody, which is a cause of allergy, is promoted by IL-4 and IL-13 but suppressed by IFN-γ. That is, Th1 cells suppress IgE production, whereas Th2 cells promote IgE production. In other words, sensitization of allergy is determined by whether Th1 cells or Th2 cells function upon exposure of antigens. It is commonly known that Th2 cells predominantly function in the patients with allergy. Allergen-specific IgE antibodies adhere to peripheral basophil and tissue mast cells. The subsequent exposure of allergen results in cross-linking of the IgE antibody on the basophil or the mast cell via the allergen. This releases inflammatory mediators including histamine, prostaglandins, and leucotriene, thereby causing an immediate allergy response. In response to these inflammatory mediators, lymphocytes, monocytes, basophils, and eosinophils are localized in the inflammatory region of the tissue and result in the release of mediators that cause various reactions including disturbance and a late phase reaction.

One way to treat a particular allergy by antigen-specifically suppressing IgE antibody production is hyposensitization therapy using an allergen protein molecule. Hyposensitization therapy can provide a long-term effect that cannot be achieved by chemotherapy, and hence, is the only treatment close to an effective therapy. However, hyposensitization therapy is not always accepted as a general method for treating allergy, possibly because its mechanism and possible side effects (such as topical swelling or anaphylactic shock) remain unknown.

In place of hyposensitization therapy, a mechanism of hyposensitization using a peptide antigen bearing a T cell epitope has been proposed. The peptide fragment carrying a T cell epitope on the allergen molecule used for this therapy contains no B cell epitope or, if any, is monovalent so that the peptide fails to cross-link an IgE receptor with high affinity on the mast cell. For these reasons, patients administered the peptide fragment should not experience side effects such as anaphylactic shock. It is further known that when T cell epitope is given in vivo, T cells are antigen-specifically inactivated (anergy) (La Salle J. M. et al.: J. Exp. Med. 176: 177–186, 1992). It is reported that based on such a theoretical background, hyposensitization using a peptide carrying major T cell epitopes of cat dander allergen Fel d1 was carried out in an experimental murine model, and T cell anergy was induced in vitro (Briner, T. J. et al.: Proc. Natl. Acad. Sci. USA, 90: 7608–7612, 1994). Clinical trials on hyposensitization using this peptide are now under way (Norman, P. S. et al.: Am. J. Respir. Crit. Care Med. 154: 1623–1628, 1996; Simons, F. E. et al.: Int. Immunol. 8: 1937–1945, 1996). Hyposensitization therapy using such a peptide carrying the major T cell epitope on the allergen molecule is called "peptide-based immunotherapy" (or "peptide-based hyposensitization therapy").

As a standard for selecting T cell epitope peptides appropriate for the peptide-based immunotherapy, a positivity index (a mean T cell stimulation index multiplied by appearance frequency) is proposed in WO 94/01560. It is also reported that in peptide design, HLA haplotypic variations in a population of patients should be covered (Wallner, B. P. & Gefter M. L.: Allergy, 49: 302–308, 1994).

DISCLOSURE OF THE INVENTION

Generally, allergic patients have specific IgE antibodies to each of two or more allergen molecules differing from each other. For a potent allergy therapy, it is important to develop a peptide-based immunotherapeutic agent effective for these patients. However, such an immunotherapeutic agent has not yet been developed. Even the idea of such an agent has never been published in any of the above literatures. Accordingly, an objective of the present invention is to provide a peptide-based immunotherapeutic agent that is efficacious even for allergy patients sensitive to two or more different allergens.

Cedar pollen contains two major allergens, Cry j 1 (Yasueda, H. et al.: J. Allergy Clin. Immunol. 71: 77–36, 1983) and Cry j 2 (Taniai, M. et al.: FEBS Letter 239: 329–332, 1988; Sakaguchi, M. et al.: Allergy 45: 309–312, 1990). More than 90% of the patients with cedar pollinosis possess specific IgE antibodies to Cry j 1 and Cry j 2; the remaining patients (slightly less than 10%) possess a specific IgE antibody to either Cry j 1 or Cry j 2 (Hashimoto, M. et al.: Clin. Exp. Allergy 25: 848–852, 1995). Use of one or more T cell epitopes from only Cry j 1 or Cry j 2 would be expected to be less effective since IgE from the patients is reactive to both Cry j 1 and Cry j 2. Thus, T cell, eptopes from both Cry j 1 and Cry j 2 should be chosen to elevate the efficacy of the peptide-based immunotherapy for cedar pollinosis. Therefore, the present inventors prepared a multi-epitope peptide containing T cell epitopes of both Cry j 1 and Cry j 2 in the same molecule. They found that the multi-epitope peptide activated T cells of patients with pollinosis in vitro but did not react with IgE antibodies of the patients. They also found that an immune response was induced in vivo using mice. Based on these new findings, the inventors found that the multi-epitope peptide in this invention is effective as a peptide-based immunotherapeutic agent for patients with cedar pollinosis.

There are many cases of cedar pollinosis that also show clinical symptoms of Japanese cypress pollens. In view of this and based on the above invention, the present inventors prepared a multi-epitope peptide containing the T cell epitopes of Japanese cypress pollen allergen Cha o 1 (Japanese Patent Application No. Hei 8-153527) and the T cell epitopes of cedar pollen allergen Cry j 1 in the same molecule. The multi-epitope peptide activated T cells of both the patients with cedar pollinosis and the patients with Japanese cypress pollinosis, though these T cells do not react with each of the T cell epitopes. The multi-epitope peptides can thus be designed for T cell epitopes derived from not only cedar and Japanese cypress pollen allergens but also other various allergens.

HLA haplotype was investigated in a group of patients (including different races) as a criterion for selecting T cell epitopes to design multi-epitopes that are effective for a broader range of patients. T cell epitope peptides were selected noting that those binding to HLA whose haplotype frequently appears in the population and those presented on different HLA class II molecules, not the same HLA class II molecule, should be selected. The thus-selected multi-epitope peptides were clarified to be effective for a wider range of patients.

The present invention includes the inventions described in each claim.

The present invention will be described below in view of designing of multi-epitope peptides effective for the patients sensitive to cedar pollens or Japanese cypress pollens or the patients sensitive to both pollens, but this invention applies to patients sensitive to other allergens as well. The technical concept of the present invention also applies to plant pollens such as short ragweed (Amb a 1, Amb a 2, Amb a 5, Amb t 5, Amb p 5), *Dactylis glomerata* (Dac g 2), and *Lolium perenne* (Lol p 1, Lol p 2, Lol p 3); tree pollens such as *Alnus glutinosa* (Aln g 1), birch tree or *Betula verrucosa* (Bet v 1, Bet v 2), mountain cedar (Jun s 1), and juniper tree (Jun v 1); and various other allergens not specifically described herein.

The "multi-epitope peptide", used herein means a peptide molecule prepared by linearly joining peptides containing T cell epitopes derived from different allergen molecules (sometimes referred to as an antigenic peptide or merely as a peptide). In this peptide, a region that is cleaved in vivo is preferably inserted between the T cell epitope-containing peptides to minimize the occurrence of epitope sites that are newly recognized. The multi-epitope peptide is finally broken down to the respective antigenic peptides at the cleavage site. When administered, it can exhibit the effect comparable to that of a mixture of these respective antigenic peptides. The cleavage site may take any structure so long as it undergoes cleavage in vivo. Examples of the cleavage site include an arginine dimer and a lysine dimer that are recognition sequences of cathepsin B, which is an enzyme localized in lysosome.

Designing of the multi-epitope peptide according to the present invention will be described with reference to cedar pollen allergens Cry j 1 and Cry j 2 as examples.

Peripheral lymphocytes collected from the patients with cedar pollinosis are stimulated by Cry j 1 or Cry j 2 to produce the T cell line for individual patient. The T cell line is stimulated by an overlapping peptide consisting of about 15 amino acids, which covers the full-length primary structure of Cry j 1 (WO 94/01560) or Cry j 2 (Komiyama, N. et al.: Biochem. Biophys. Res. Commun. 201: 1201, 1994) to identify the antigenic peptides containing T cell epitopes in the Cry j 1 or Cry j 2 sequence (FIGS. 1 and 2).

Next, typing is performed for HLA class II molecules which bind to these antigenic peptides.

In humans, three different molecules, regions DR, DQ, and DP, exist as gene products of the HLA class II. This suggests that differentiation of T cells would be restricted by antigen-presenting molecules DR, DQ, and DP. The T cell clones established for each, patient are used to determine by which locus-derived antigen-presenting molecules the antigenic peptide of Cry j 1 or Cry j 2 is presented. They also determine whether the T cells that have received antigenic peptide information via DR, DQ or DP molecules tend to be differentiated into Th1 cells or Th2 cells. Such a typing is performed using the T cell clone established for individual patients (FIGS. 3 and 4).

FIGS. 3 and 4 clearly show that differentiation into Th1, Th2 or Th0 of the T cells stimulated by the antigenic peptide is not restricted by a specific epitope or a specific combination of HLA molecules. In selecting a peptide for designing the multi-epitope peptide of the present invention, any peptide can be a candidate for the antigenic peptide since any T cell epitope-containing peptide can stimulate T cells.

The criteria for selecting peptides to design the multi-epitope peptide of the present invention are as follows:

(1) Peptides are selected in the order of a positivity index (WO 94/01560) (peptides having a positivity index of 100 or more should be selected).

(2) Peptides presented on HLA class It molecules that frequently appear as antigen-presenting molecules are selected.

(3) Where there is no significant difference in the positivity index, peptides presented by restriction molecules of different types are selected to enhance the effectiveness. Specifically, in selecting a T cell epitope of an allergen that causes a certain allergic disease, the HLA haplotype in a group of patients with the allergy is first examined, and a T cell epitope restricted by an HLA haplotype whose gene frequency is high in the population to which the patient group belongs is selected. This is then the best selection that should achieve the best effect in that patient group. However, the thus-selected T cell epitope may not be effective at all in other patient groups.

Taking HLA haplotype DPB1*10501 as an example, it is assumed that this HLA haplotype is quite frequently observed in Japanese patients with a certain allergic disease, and the HLA haplotype-restricting T cell epitope is selected. The thus-selected peptide would hardly be effective for Northern American patients with the same allergy because the gene frequency of the HLA haplotype is as much as 39.0% in Japanese patients, whereas it is as little as 1.3% in white Americans and 0.8% in African Americans in Northern America. For Northern American patients, the HLA-DP restricting T cell epitope DPB1*0401 (in Northern America, 30.2% for white American patients and 11.1% for African American patients; 4.8% for Japanese patients) should be selected. It is also important to select a peptide presented on the antigen-presenting molecules differing in the locus level like DR, DQ, or DP; even though the loci are the same, it is important to select a peptide presented on the antigen-presenting molecules having different haplotypes.

In this case, the preferable epitope site contains no cysteine residue. When the epitope site contains a cysteine residue, the residue might bind non-specifically to HLA class II molecules. When immunized with an antigenic peptide containing a cysteine residue, the site that is originally not an antigen might be recognized as a new epitope. When such a peptide is recognized as an epitope, the cysteine-containing epitope is recognized by the peptide repeatedly through its second and third administrations, which may possibly cause side effects.

Specific embodiments of designing the multi-epitope will be described below. According to the positivity index of Cry j 1 and Cry j 2 shown in FIGS. 1 and 2, the T cell epitope of Cry j 1, Peptide No. 43 with amino acid residues at positions 211–225 (hereinafter abbreviated as p211–225) (restriction molecules DPA1*0101 to DPB1*0501) shows the highest positivity index and Peptide No. 22, p106–120 (restriction molecule DRB5*0101) shows the second highest positivity index. These two peptides are selected as the antigenic peptides to be used in the multi-epitope peptide. Turning to Cry j 2, Peptide No. 14, p66–80 (restriction molecule DRB5*0101) and Peptide No. 38, p186–190 (DRB4*0101) show the highest positivity indexes. Likewise, these two peptides can be selected as the antigenic peptides. Peptide No. 37, p181–195, located before Peptide No. 38 in Cry j 2 has a high positivity index of 280, but its restriction molecules are DPA1*0101 to DPB1*0201, which differ from the restriction molecule of Peptide No. 38. Since Peptide No. 37, p181–195 overlaps with Peptide No. 38, p186–200 by 10 residues, 5 residues from No. 37 are added ahead to No. 38. The thus-designed peptide can be selected as an HLA-DP restricting peptide. Peptides as selected above do not restrict DQ. Restriction molecules for Peptide No. 4, p16–30 of Cry j 1, are DQA1*0102 to DQB1*0602, but a cysteine residue is contained at the center of the epitope. Thus, Peptide No. 4 cannot be selected. In Cry j 2, p341–360, corresponding to Peptide Nos. 69–70, is a peptide presented on DQA1*0102 to DQB1*0602. Peptide No. 70 also contains cysteine, whereas T cells can be activated by only the cysteine-free Peptide No. 69. Thus, 12 residues, p344–355 (ISLKLTSGKIAS, SEQ ID NO. 6) be selected. Peptide No. 22, p106–120 of Cry j 1 contains cysteine at position 107. At least nine residues of p109–117 (FIKRVSNVI, SEQ ID NO. 7) are required for determining the T cell epitope core sequence using a T cell clone. Thus, if Pro-Cys residues at p106–107 are removed, the remaining peptide can be used.

The antigen taken up into the antigen-presenting cells is degraded in lysosome. How the foreign proteins taken up into the antigen-presenting molecules are processed and how they are bound to HLA class II molecules are still unknown. However, it is reported that cathepsin B participates in the digestion of antigens in this complicated mechanism (Katsunuma, N.: Nihon Men-Eki Gakkai (Japanese Society of Immunology) 25: 75, 1995).

With respect to several HLA class II types, an HLA-binding amino acid motif of the antigenic peptide has been determined. Binding to HLA class II molecules has specificity, but numerous antigenic peptides can bind to specific HLA class II molecules if the peptides meet a certain criterion (Rammensee, H. G. et al. Immunogenetics. 41: 178–228, 1995). For this reason, a newly recognized epitope site might possibly be created in the antigenic peptide-binding site. To avoid this, the multi-epitope peptide should be designed so as to be cleaved into each of the antigenic peptides in the antigen-presenting cells. The peptide sequence recognized by cathepsin B is the Arg-Arg-hydrophobic sequence or the Lys-Lys-hydrophobic sequence. Therefore, Arg-Arg or Lys-Lys is added to the latter half of the peptide containing the epitope and, in the following epitope sequence, a hydrophobic amino acid sequence is placed after Arg-Arg or Lys-Lys.

Since Arg-Arg is inserted between the antigenic peptides, the order of the antigenic peptides in this specific embodiment is considered insignificant. When Arg is linked to the latter half of Peptide No. 14 of Cry j 2 (FIG. 2), however, Tyr at position 73 becomes a first anchor. The Arg residue added then becomes amino acid residue at position 9 in the peptide motif of DRB5*0101 and serves as a second anchor. Thus, the Arg residue may be recognized as a new epitope. Therefore, this sequence should be located at the end of the multi-epitope peptide.

The thus-obtained multi-epitope peptide is shown as SEQ NO: 1. The restriction molecules for this multi-epitope are DRB4*0101, DRB5*0101, DPA1*0101–DPB1*0201, DPA1*0101–DPB1*0501, and DQA1*0102–DQB1*0602. In The 11th International Histocompatibility Workshop, the frequency of these genes was calculated in the Japanese population (Tsuji, K. et al.: HLA 1991, vol. 1, 1992, Oxford University Press) and found to be 0.291 for DRB4*0101, 0.056 for DRB5*0101 (0.070 for DRB5*0102), 0.208 for DPB1*0201, 0.399 for DPB1*0501, and 0.053 for DQB1*0602 (0.204 for DQB1*0601). Based on these data, the antigen frequency is calculated to be 0.50 for DRB4*0101, 0.11 for DRB5*0101 (0.14 for DRB5*0102), 0.37 for DPB1*0201, 0.64 for DPB1*0501, (0.79 according to Hori et al.), and 0.10for DQB1*0602 (0.37 for DQB1*0601). Since DRB5*0101 and DQB1*0602 are regarded as identical due to the presence of linkage disequilibrium, the data of DRB5*0101 is used for DQB1*0602. The probability that the Japanese population carries both DPB1*0201 and DPB1*0501 or either one is calculated to be 0.85. Similarly, the probability that the Japanese population carries both of DRB4*0101 and DRB5*0101 or either one is calculated to be 0.56. From these values, about 90% of patients are estimated to recognize more than one T cell epitope contained in the multi-epitope peptide of SEQ NO: 1. However, it is unclear whether the patients with these HLA types possess a T cell repertory capable of recognizing these epitope peptides presented on these restriction molecules. Furthermore, the number of epitopes that cause proliferation of T cells is unknown (two or more epitopes would be necessary). Thus, the efficiency of the multi-epitope peptide might decrease. In practice, it is properly assumed to be approximately 77% based on the result of testing proliferation response of peripheral lymphocytes from 17 patients.

To increase the range of patients to be effectively treated, the multi-epitope peptide can also be designed to carry more T cell epitopes than described above. Examples of such multi-epitope peptides include one prepared by joining p213–225 and p108–120 of Cry j 1, p182–200 and p79–98 of Cry j 2, p80–95 of Cry j 1, and p66–80 of Cry j 1, in this order (SEQ NO: 2), and one prepared by joining p213–225 and p108–120 of Cry j 1, p182–200 and p79–98 of cry j 2, p67–95 of Cry j 1, and p238–251 and p66–80 of Cry j 2, in this order (SEQ NO: 3). These multi-epitope peptides are effective as peptide-based immunotherapeutic agents since the peptides stimulated all the peripheral lymphocyte samples from the 21 tested patients with cedar pollinosis but did not react with the IgE antibody of the patients. Developing this concept, the effectiveness can be improved by preparing a T cell epitope containing allergens of different species, e.g., both Japanese cypress pollen allergen and cedar pollen allergen, by the method described in Example 13.

The present invention also includes modification of the antigenic peptide region used in the multi-epitope peptide to regulate the activity of T cells. The "modification" used herein means substitution, deletion, and insertion of at least one amino acid residue. Changes of properties of T cells imparted by amino acid substitution in the antigenic peptide can be examined by known methods. For example, 1) a certain amino acid of the multi-epitope peptide of the present invention is substituted with an analogous amino acid, e.g., by substituting Asp with Glu, Asn with Gln, Lys with Arg, Phe with Tyr, Ile with Leu, Gly with Ala, and Thr with Ser, to produce analog peptides, which are compared with the original peptide in T cell proliferating ability or lymphokine-producing ability. Alternatively, 2) a certain amino acid of the multi-epitope peptide is substituted with a non-analogous amino acid, for example, by substituting a polar amino acid or a hydrophilic amino acid with a hydrophobic amino acid Ala, and a hydrophobic amino acid with a hydrophilic amino acid Ser, and the property of the modified peptide is compared to that of the original peptide. The present invention also includes the thus-prepared multi-epitope analog peptides that are immunologically equivalent to the multi-epitope peptide of the present invention in terms of the positivity index and the T cell activation ability.

Most T cells that react with the antigenic peptide derived from Cry j 1 or Cry j 2 possess the properties of Th2 and Th0 in combination (FIGS. 3 and 4) BCG vaccine can potentiate the cellular immune activity to prevent infection with *tubercle bacillus*. To potentiate cellular immunity, T cells of Th1 type should be induced. It is reported that studies on the property of a human T cell clone with BCG inoculation revealed an increased level of Th1 type T cells (Matsushita, Sho, The 45th Japanese Association of Allergy, 836, 1995). According to Matsushita, there is a Th1 clone that is restricted by HLA-DR14 (DRB1*140) and that recognizes 84–100 amino acid sequence (EEYLILSARDVLAVVSK, SEQ ID NO. 8) of BCGA protein. If the HLA haplotype DPA1–DPB1*0501-restricting T cell epitope that is possessed by more than 60% of Japanese population is selected (for example, Peptide No. 43 (p211–225)/ KSMKVTVAFNQFGPN (SEQ ID NO. 9) of Cry j 1 shown in FIG. 1), this peptide is bound to the 84–100 T cell epitope of *tubercle bacillus* BCGa protein restricted by DRB1*1405. It is highly likely that the thus-prepared multi-epitope peptide EEYLILSARDVLAVVSKRRMKVTVAFNQFGPN (SEQ ID NO. 10) would be quite efficacious for patients with cedar pollinosis carrying haplotype DRB1*1405. The use of such a multi-epitope peptide would lead to production of Th1 lymphokines, especially IL-12, by a peptide derived from BCGA antigen. It is known in several cases in humans and mice that IL-12 has an activity contradictory to that of IL-4 and acts on T cells to induce differentiation of Th cells to Th1 (Manetti, R., et al.: J. Exp. Med., 177, 1199–1204, 1993; Wu, C., et al.: J. Immunol., 151, 1938–1949, 1993; Hsieh, C. , et al.: Science, 260, 547–549, 1993). In particular, the experimental results by Manetti et al. indicate that a T cell clone specific to Der p1 antigen, a mite allergen, basically induces Th2 but induces Th1 or Th0 in the presence of IL-12. Thus, using the multi-epitope peptide prepared by joining a T cell epitope having Th1 induction activity to an allergen-reactive T cell epitope, T cells that are inherently induced to Th2 would be induced to Th1 or Th0.

When the peptide of the present invention containing at least one T cell epitope of Cry j 1 and/or Cry j 2 is subcutaneously administered to a mouse, which is then exposed to cedar pollen allergen, T cell anergy occurs (FIGS. 13 and 14), and IL-2 production is significantly reduced as compared to the control group. It is reported that hyposensitization therapy reduces IL-2 in humans (J. Allergy Clin. Immunol. 76: 188, 1985). Furthermore, the multi-epitope peptide of the present invention can activate each of the peptide-constituting T cell clones to the T cell epitope peptides (FIG. 10) but does not react with IgE antibodies of the patients (FIG. 8). These results show that the multi-epitope peptide of the present invention induces immune tolerance against allergens and is effective as a peptide-based immunotherapeutic agent for allergic diseases. The multi-epitope peptide of the present invention may be administered together with pharmaceutically acceptable carriers or diluents. The effective dose of the multi-epitope peptide may vary depending upon sensitivity to cedar pollen allergen, age, sex, and the body weight of the patients and other factors such as ability of a peptide to induce immune response in the patients.

The multi-epitope peptide may be administered in a simple manner using an administration route including injection (subcutaneous or intravenous), rhinenchysis, instillation, oral administration, inhalation, percutaneous administration, etc.

The one-letter notation for amino acids used in the specification and the sequence listing follows the definition prescribed by IUPAC, Commission on Biochemical Nomenclature (cf., Biochemical Dictionary, 2nd ed., 1468, Table 1.1).

BRIEF DESCRIPTION OF DRAWINGS

FIG. 3 shows the Th type of the T cell clones that recognize complexes between the Cry j 1 antigenic peptides and HLA class II molecules as well as the Th types of the HLA class II molecules.

FIG. 4 shows the Th type of T cell clones that recognize complexes between the Cry j 2 antigenic peptides and HLA class II molecules as well as the Th types of the HLA class II molecules.

FIG. 7 shows the amino acid sequences used (SEQ ID NO: 157–161) in the multi-epitope peptide. In this figure, Peptides a and b correspond to Peptide Nos. 43 and 22 of Cry j 1, respectively; Peptide c corresponds to No. 14 of Cry j 2; and Peptides d and e correspond to Peptide Nos. 37–38 (p18–200) and Nos. 69–71 (p346–365), respectively.

FIG. 8 shows the reactivity of the multi-epitope peptides designated as C.A.#1, C.A.#2, C.A.#3, C.A.#4, C.A.#5 and C.A.#6 with human IgE.

FIG. 15 shows core amino acid sequencing of Peptide No. 22 (p106–120) of Cry j 1 (SEQ ID NO: 162–173).

FIG. 16 shows the reactivity of T cell lines of the patients with cedar pollinosis and the patients with hinoki pollinosis with the multi-epitope peptide prepared by binding a cedar pollen-specific T cell epitope peptide to a Japanese cypress pollen-specific T cell epitope peptide.

BEST MODE FOR IMPLEMENTING THE INVENTION

EXAMPLE 1

Identifying T Cell Epitope of Cry j 1 and Cry j 7 Using T Cell Line

Peripheral lymphocytes from 18 patients with cedar pollinosis were stimulated by cedar pollen allergen Cry j 1 or Cry j 2 to establish the T cell line of each patient capable of specifically recognizing the respective allergen.

A mixture of $5 \times 10^4$ cells of the autologous B cell line treated with mitomycin C, 2 $\mu$M of an overlapping peptide, and $2 \times 10^4$ cells of the T cell line was incubated for 2 days in RPMI-1640 medium supplemented with 0.2 ml of 15% serum on a 96-well culture plate. After 0.5 $\mu$Ci [$^3$H] thymidine was added to the medium, incubation was continued for a further 18 hours. After the cells were harvested on a glass filter using a cell harvester, the level of [$^3$H] thymidine taken up into the cells was determined with a liquid scintillation counter. If the stimulation index is 2 or more, we consider that the added peptide is recognized as an antigenic peptide. The stimulation index means a value obtained by dividing the level of [$^3$H] thymidine taken up into the cells when the peptide was added by the level of [$^3$H] thymidine taken up into the cells when no peptide was added.

For Cry j 1, the number of T cell epitopes on the Cry j 1 molecule that each patient recognized was on average 9.8 and ranged from 4 to 15. For Cry j 2, the number of T cell epitopes was on average 8.7 and ranged from 2 to 13. Cry j 1 consists of 353 amino acids, and, Cry j 2, 379 amino acids. Therefore, it was estimated that 2.3 to 2.8 T cell epitopes are present per 100 amino acid residues.

The HLA class II type is considered to vary in every patient. It is thus assumed that a T cell epitope to be recognized would vary depending on the HLA class II type. For this reason, the antigenic peptide that the patients recognized was mapped for the individual patient. The results indicate that the epitopes on the Cry j 1 and Cry j 2 molecules differ depending on the patient. On the allergen molecule, there are both regions that can be readily recognized and regions that can hardly be recognized, as a T cell epitope, depending on individuals. Moreover, since the proliferation rate of T cells varies depending on a T cell epitope, the epitope map alone makes it difficult to determine what antigenic peptide should be chosen to design the multi-epitope peptide. Therefore, eighteen patients were further examined with respect to the antigenic peptide which showed a stimulation index of 2 or more. A mean stimulation index of the antigenic peptide was calculated and multiplied by the rate of patients carrying the antigenic peptide (frequency in appearance) to calculate the "positivity index" which shows the predominate order for the respective epitopes (cf. WO 94/01560).

Figure 1:
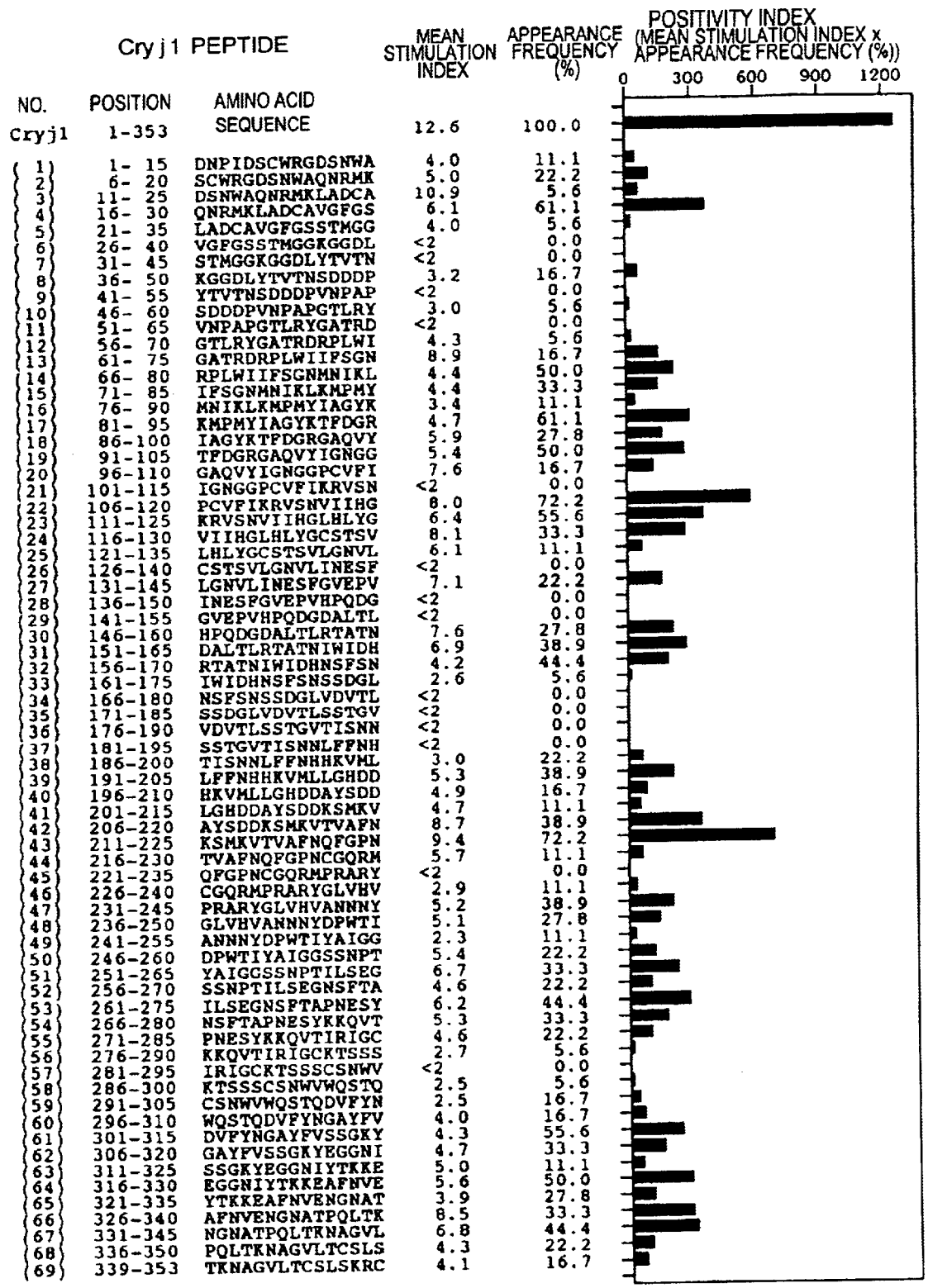
FIG. 1 shows a mean stimulation index, frequency of appearance, and a positivity index (mean stimulation index multiplied by frequency of appearance) of the cell line derived from the patients with cedar pollinosis, against Cry j 1 overlapping peptides (SEQ ID No: 15–83).
Figure 2:
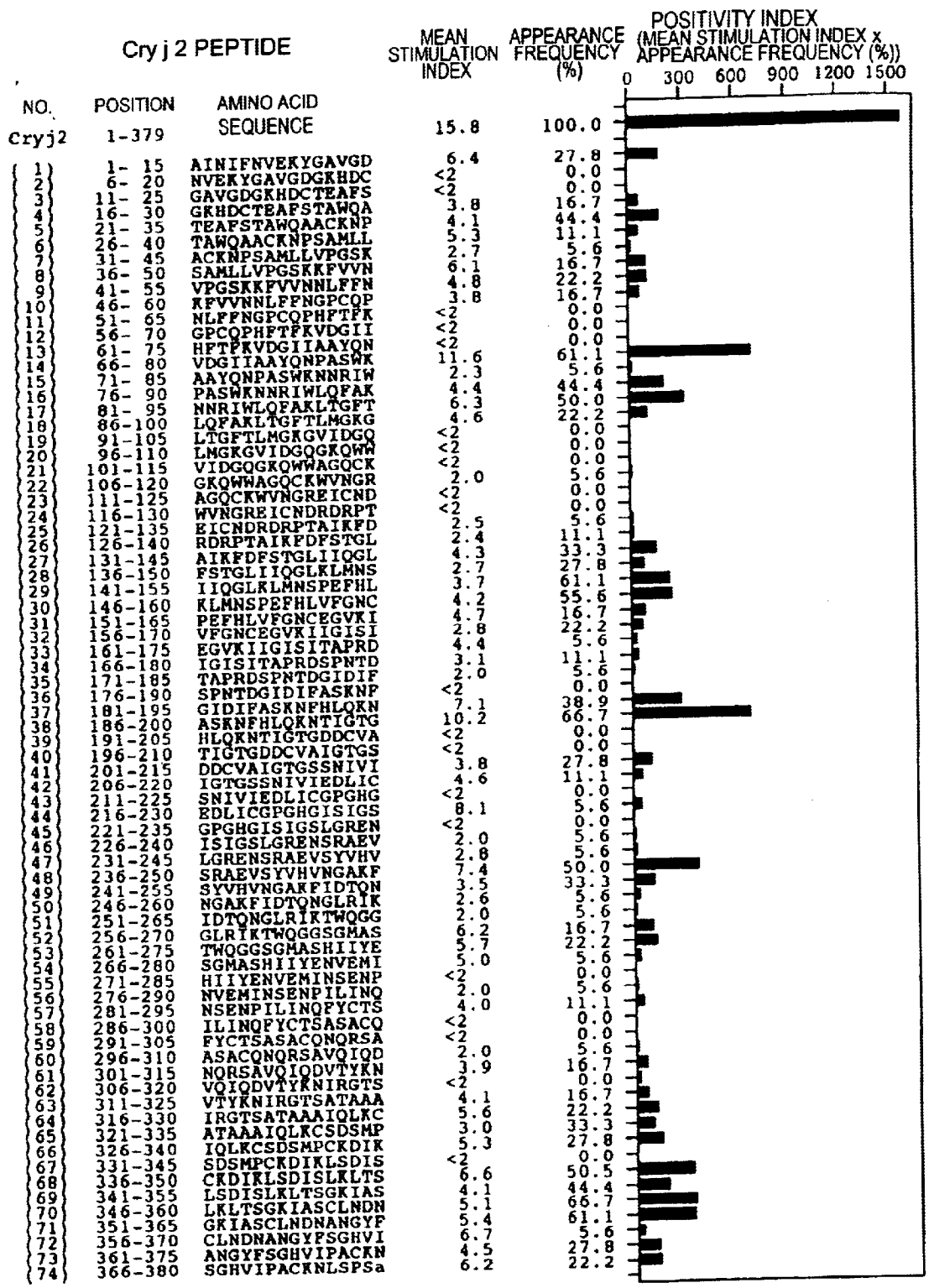
FIG. 2 shows a mean stimulation index, frequency of appearance, and a positivity index (mean stimulation index multiplied by frequency of appearance) of the cell line derived from the patients with cedar pollinosis, against Cry j 2 overlapping peptides (SEQ ID NO: 84–156)

The results are shown in FIGS. 1 and 2. In Cry j 1, Peptide No. 43 (p211–225) shows the highest positivity index, 679, which is followed by the second highest Peptide No. 22 with a positivity index of 578 and Peptide No. 4 with a positivity index of 373. In Cry j 2, Peptide No. 14 shows the highest positivity index (709). Peptide No. 38 with a positivity index of 680 and Peptide No. 48 with a positivity index of 370 then follow. One antigenic peptide having a high positivity index may be selected and used for the peptide-based immunotherapy. However, even for the highest appearance frequency, the effect can be theoretically expected in only 72% of the patients, and the actual efficiency would be lower. To increase the efficiency, it is necessary to use numerous T cell epitopes in combination. In this case, T cell epitopes with a high positivity index are chosen as candidates. However, just using epitopes with a high positivity index alone cannot increase the efficiency if HLA class II molecules presenting these epitopes as antigens are same. It is thus necessary to identify the type of HLA class II molecules presenting T cell epitope peptides.

EXAMPLE 2

Identifying T Cell Epitope Peptide Recognized By T Cell Clone

Two patients, Patient B (PB) and Patient J (PJ), who recognize Peptide Nos. 43 and 22 showing a high positivity index in Cry j 1 and three patients, PB, Patient C (PC), and Patient R (PR), who recognize Peptide Nos. 14, 38, 48, and 69 showing a high positivity index in Cry j 2 were selected from the eighteen patients with cedar pollinosis. Peripheral lymphocytes from these patients with cedar pollinosis were stimulated by Cry j 1 or Cry j 2 to establish T cell clones capable of recognizing Cry j 1 or Cry j 2. The types of HLA class I and class II molecules of the four patients are shown below.

| PB: | A2/24 - B39/55 - Cw7/w3 - DRB1*1501/0901 - DRB4*0101-DRB5*0101, DQA10102/0301 - DQB1*0602/0303 - DPA1*0101/0101 - DPB1*0501/0201; |
|---|---|
| PJ: | A24/- - B61/51 - Cw3/- - DRB1*1501/0802 - DRB5*0101, DQA1*0102/0401 - DQB1*0602/0402 - DPA1*-/- - DPB1 0501/0402; |
| PC: | A-2/2 - B54/51 - Cw1/-, DRB1*0405/1501 - DRB4*0101 - DRB5*0101 - DQA1*0301/0102 - DQB1*0401/0602 - DPA1*0202/0202 - DPB1*0201/0501; |
| PR: | A-11/- - B60/35 - Cw7/w3 - DRB1*0901/1501 - DRB4*0101 - DRB5*0101 - DQA1*0301/0102 - DQB1*0303/0602 - DPA1*01/0202 - DPB1*0201/0201. |

Thirty-five T cell clones in total that specifically recognize Cry j 1 were established from the peripheral lymphocytes derived from PB, and 14 similar T cell clones from PJ. Likewise, 31 T cell clones, 10 T cell clones, and 17 T cell clones in total that specifically recognize Cry j 2 were established from the peripheral lymphocytes derived from PB, PC and PR, respectively. Since these T cell clones were all CD3$^+$, CD4$^+$, CD8$^{31}$, TCRαβ$^+$ and TCRγδ$^-$, the restriction molecules were found to be HLA class II molecules. A mixture of 5×10$^4$ cells of the autologous B cell line previously treated with mitomycin C, 2 μM of an overlapping peptide, and 2×10$^4$ cells of the T cell clone was incubated for 2 days in RPMI-1640 medium supplemented with 0.2 ml of 15% serum on a 96-well micro culture plate. After 0.5 μCi [$^3$H ] thymidine was added to the medium, incubation was continued for a further 18 hours. After the cells were harvested on a glass filter using a cell harvester, the level of [$^3$H] thymidine taken up into the cells was determined using a liquid scintillation counter. By this procedure, the T cell epitope recognized by each of the T cell clones was identified.

In the T cell clones that recognized Cry j 1, 69% (34/49) showed a proliferation response by stimulation with the peptides and, as a result, the epitopes were identified. Similarly, the antigenic peptide could be identified in 69% (40/58) out of the T cell clones which recognized Cry j 2. The T cell clones capable of specifically recognizing Cry j 1 recognized Peptide Nos. 4, 13, 19, 22, 30, 31, 39, 43, 51, and 66, and the T cell clone capable of specifically recognizing Cry j 2 recognized Peptide Nos. 4, 8, 14, 17, 31, 37, 38, 48, 65, 66, 68, 69, and 70. The results are summarized in FIGS. 3 and 4.

EXAMPLE 3

Identifying HLA Class II Restriction Molecules at the Locus Level

HLA class II restriction molecules were identified at the locus level by adding a monoclonal antibody capable of specifically reacting with DR, DQ or DP of HLA class II molecules to the proliferation response system of the T cell clones established in Example 2, thereby inhibiting the proliferation response of T cells.

Figure 5:
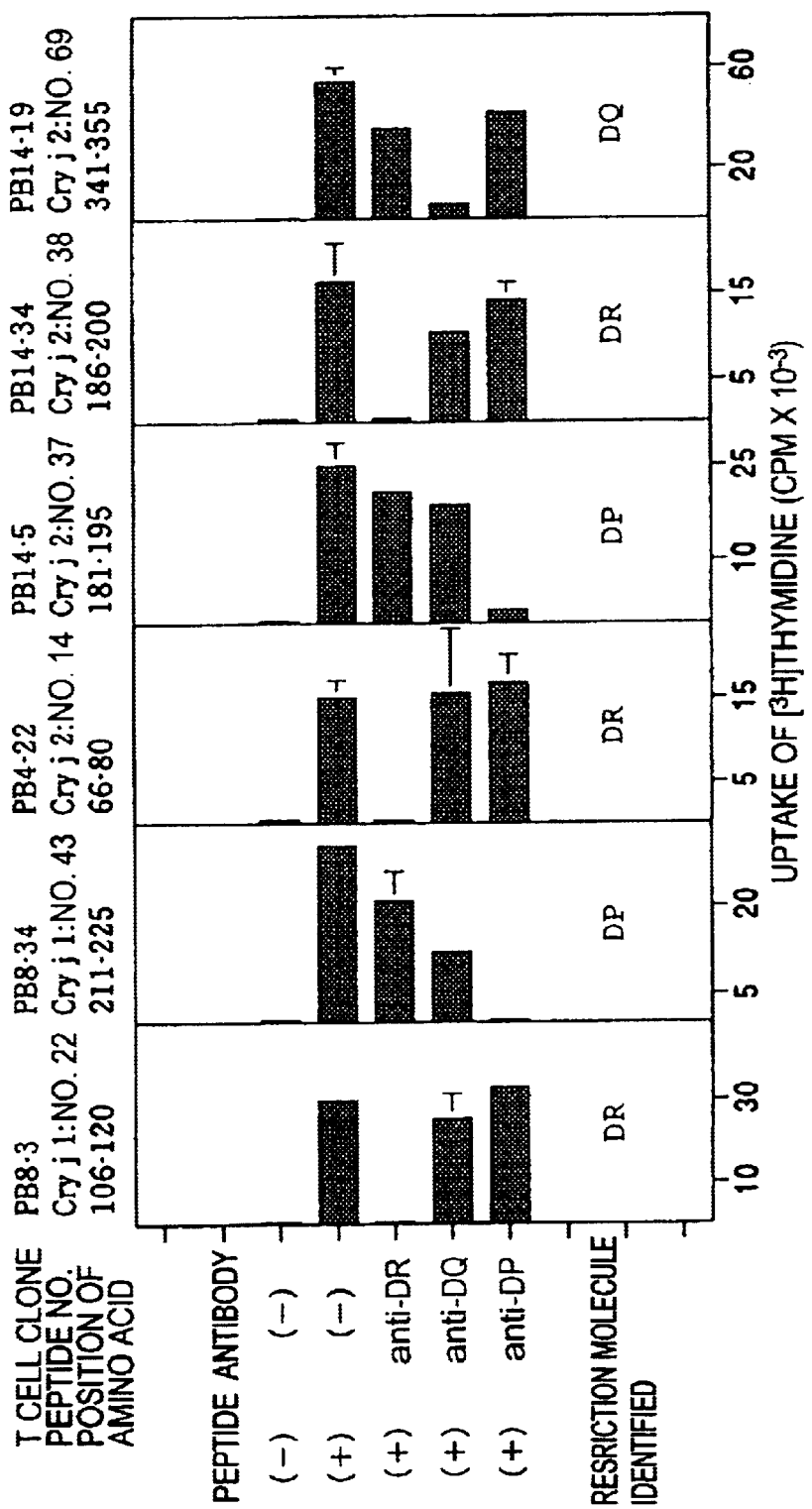
FIG. 5 shows the results of identifying HLA class II molecules capable of binding to an antigenic peptide at the locus level (DR, DQ, and DP).

A mixture of 2×10$^4$ cells of the autologous B cell line previously treated with mitomycin C; 2 μM of an overlapping peptide; 3 μg/ml of anti-DR, -DQ or -DP monoclonal antibody (manufactured by Becton Dickinson Inc.); and 2×10$^4$ cells of the T cell clone was incubated for 2 days in RPMI-1640 medium supplemented with 0.2 ml of 15% serum on a 96-well micro culture plate. After 0.5 μCi [$^3$H] thymidine was added to the medium, incubation was continued for a further 18 hours. After the cells were harvested on a glass filter using a cell harvester, the level of [$^3$H] thymidine taken up into the cells was determined using a liquid scintillation counter. The results shown in FIG. 5 indicate that the restriction molecule of the Cry j 1 p106–120, Cry j 2 p66–80 and Cry j 2 p186–200 peptides was DR; that of the Cry j 2 p341–355, peptide was DQ; and that of the Cry j 1 p211–225 and Cry j2 p118–195 was DP. The restriction molecules of other T cell clones were analyzed in the same manner (cf. FIGS. 3 and 4).

EXAMPLE 4

Identifying the HLA Class II Restriction Molecules

HLA class II restriction molecules can be identified using the T cell clones whose restriction molecules were identified at the HLA class II locus level and, as antigen-presenting cells, mouse L-cells transfected with each type for DR and B cell line having the same haplotype for DQ or DP.

A mixture of 5×10$^4$ mouse L cells previously treated with mitomycin C of the B cell line coincident in haplotype; 2 μM of an overlapping peptide; 3 μg/ml of anti-DR, -DQ or -DP monoclonal antibody (manufactured by Becton-Dickinson Inc.); and 2×10$^4$ cells of the T cell clone was incubated for 2 days in RPMI-1640 medium supplemented with 0.2 ml of 15% serum on a 96-well micro culture plate. After 0.5 μCi [$^3$H] thymidine was added to the medium, incubation was continued for a further 18 hours. After the cells were harvested on a glass filter using a cell harvester, the level of [$^3$H] thymidine taken up into the cells was determined using a liquid scintillation counter.

Figure 6:
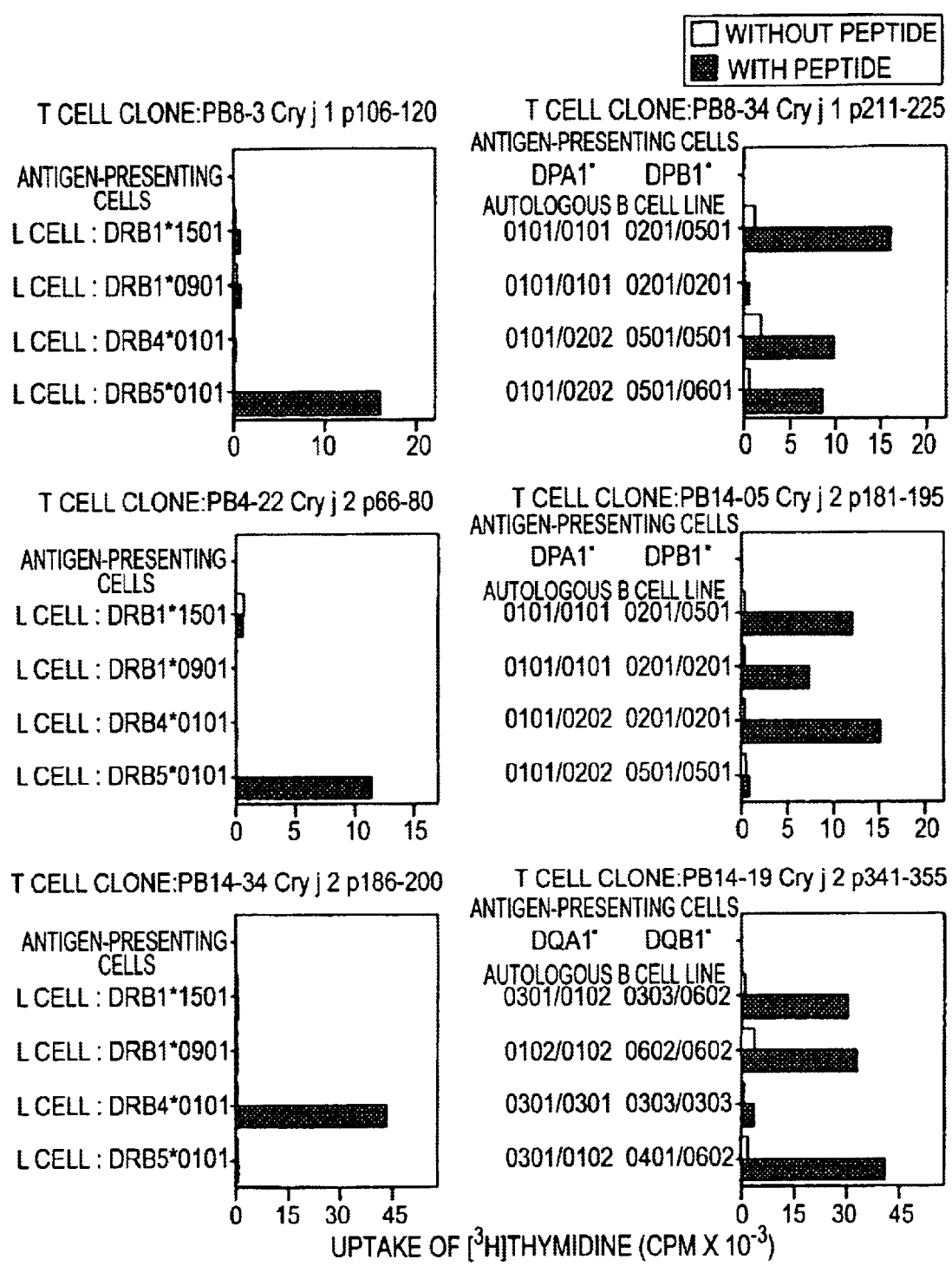
FIG. 6 shows the results of identifying HLA class II molecules capable of binding to an antigenic peptide at an allelic level of each locus.

The restriction molecules can be identified by observing the proliferation response of T cell clones. The Cry j 1 p106–120 peptide-presenting restriction molecule was DRB5*0101, the Cry j 1 p211–225 peptide-presenting restriction molecule was DPA1*0101–DPB1*0501, the Cry j 2 p66–80peptide-presenting restriction molecule was DRB5*0101, the Cry j 2 p181–195 peptide-presenting restriction molecules was DPA1*0101–PDB1*0201, the Cry j 2 p186–200 peptide-presenting restriction molecules was DRB4*0101, and the Cry j 2 p341–355 peptide-presenting restriction molecules was DQA1*0102–DQB1*0602 (FIG. 6). The results obtained with the other epitope sites are shown in FIGS. 3 and 4.

EXAMPLE 5

Identifying the Type of T Cell Clone

Th2 cells are considered to participate in the development of allergy. The current level of investigations has not completely clarified if differentiation of T cells into Th1 or Th2 cells is restricted, after antigen stimulation, by a specific epitope peptide or on a HLA class II locus level. When Th2 cells are predominantly induced after stimulation with a peptide, it is highly likely that administration of the peptide will worsen the cedar pollinosis. The T cell clones prepared in Example 2 were stimulated with the epitope peptide recognized by T cells. Th type was determined by measuring the amount of IL-2, IL-4, and IFN-γ produced.

A mixture of 1×10$^5$ cells of the autologous B cell line previously treated with mitomycin C, 2 μM of the epitope peptide, and 5×10⁵ cells of the T cell clone was incubated for 24 hours in RPMI-1640 medium supplemented with 1 ml of 10% human serum on a 24-well micro culture plate. The cells were precipitated by centrifugation to obtain the culture supernatant. IL-2, IL-4, and IFN-γ in the supernatant were determined using the respective ELISA kits commercially available [for IL-2, manufactured by R & D Inc.; for IL-4, manufactured by Medgenics Inc.; and for IFN-γ, manufactured by Otsuka Assay Research Laboratories).

The amounts of IL-2, IL-4, and IFN-γ produced by each T cell clone are shown in FIGS. 3 and 4. The T cell clones which recognize Cry j 1 were twelve Th2, one Th1, and sixteen Th0 cells, showing that there were more Th2 clones than Th1 clones. In contrast, the T cell clones which recognize Cry j 2 were ten Th2, eight Th1, and eight Th0 cells, showing that the number of Th2 clones was roughly equal to the number of Th1 clones. A comparison of T cell epitopes recognized by the respective T cell clones, restriction molecules, and Th type reveals that the Th2, Th1 or Th0 type varies depending upon each T cell clone. Both Th2 cells and Th1 cells are found in a few T cell clones which recognize the same epitope and the same antigen-presenting molecule. These results indicate that after stimulation with Cry j 1 or Cry j 2, differentiation of T cells into Th2, Th1 or Th0 is not controlled by the combination of a specific T cell epitope and a specific restriction molecule. In other words, all of the peptides carrying the T cell epitope sites can be candidates for the multi-epitope peptide of the present invention.

EXAMPLE 6

Preparing the Multi-epitope Peptide

Identifying the IgE antibody epitope sites present on Cry j 1 and Cry j 2 reveals that Cry j 1 lacks an IgE epitope capable of recognizing the primary structure and at least four IgE antibody epitope sites are present on Cry j 2. However, these IgE antibody epitope sites differ from the epitope sites of T cells. Based on this finding, the peptides shown in FIG. 7 were selected from the T cell epitopes of Cry j 1 and Cry j 2.

Peptides a and b shown in FIG. 7 correspond respectively to Peptide Nos. 43 and 22 of Cry j 1 shown in FIG. 1, Peptide c corresponds to No. 14 of Cry j 2 shown in FIG. 2, and Peptides d and e respectively consist of a part of the amino acids 37–38 and 69–71 of Cry j 2 shown in FIG. 2.

These six peptides were joined to each other in tandem to prepare the multi-epitope peptide of the present invention. In this case, the two peptides a and b were joined in the order of a and then b; the remaining three peptides (Peptides c, d and e) were joined at random. The sequence Arg-Arg was inserted between the peptides. Thus, the following six multi-epitope peptides were produced:

C.A.#1. a-Arg-Arg-b-Arg-Arg-c-Arg-Arg-e-Arg-Arg-e

C.A.#2. a-Arg-Arg-b-Arg-Arg-c-Arg-Arg-e-Arg-Arg-d

C.A.#3. a-Arg-Arg-b-Arg-Arg-d-Arg-Arg-c-Arg-Arg-e

C.A.#4. a-Arg-Arg-b-Arg-Arg-d-Arg-Arg-e-Arg-Arg-c

C.A.#5. a-Arg-Arg-b-Arg-Arg-e-Arg-Arg-c-Arg-Arg-d

C.A.#6. a-Arg-Arg-b-Arg-Arg-e-Arg-Arg-d-Arg-Arg-c

EXAMPLE 7

Reactivity of the Multi-epitope Peptides with Human IgE Antibody

The six multi-epitope peptides (C.A.#1 through C.A.#6) obtained in Example 6 were dissolved in 0.2 M acetate buffer solution (pH 4.5). The solution was dispensed in quantities of 0.1 ml/well in a black plate (manufactured by Dainihon Pharmaceutical Co., Ltd.) then allowed to stand at 4° C. overnight. After the antigen solution was removed, the wells were washed three times with a washing solution and the serum (4-fold dilution) from 29 patients with cedar pollinosis and healthy subjects were each added to separate wells. The system was then reacted at 37° C. for 4 hours. After the sera were removed, the wells were washed three times with a washing solution then reacted with anti-human IgE antibody (made by Pharmacia Inc.) at room temperature overnight. After washing three times with a washing solution, a substrate solution containing 0.1 mM 4-methylumbelliferyl-, β-D-galacto-pyranoside/0.01 M phosphate buffer (pH 7.0), 0.1 M NaCl, 1 mM MgCl₂, 0.1% NaN, and 0.1% BSA was added, and the solution was incubated at 37° C. for 2 hours. A solution of 0.1 M glycine/NaOH (pH 10.3) was added to the wells to terminate the reaction. Fluorescent intensity was measured using a fluorophotometer (Labsystems). For positive control to each multi-epitope peptide, biotin-labeled rabbit anti-d epitope IgG and peroxidase-labeled streptoavidin (made by Pierce Inc.) were reacted.

As a result, all sera from the 29 human subjects exhibited a fluorescent intensity of 3 to 5 to all of the six multi-epitope peptides (C.A.#1 through #6) (blank: 3 or 4). In contrast, when the antigen Cry j 1 extracted and purified from cedar pollen was used, a fluorescent intensity of 1,000 or more was noted in six subjects, 100 or more in 14 subjects, 10 or more in four subjects and nine or less in five subjects. In contrast, rabbit anti-d epitope peptide IgG exhibited a fluorescent intensity of 3,000 or more in response to the six consensus allergens (blank: 112; 230 to Cry j 1 allergen). These results reveal that the order of joining each epitope site in the multi-epitope peptide does not affect the reactivity with human IgE antibody (FIG. 8).

EXAMPLE 8

Recognizing the T Cell Epitopes in the Multi-epitope Peptide

The antigenic peptide constituting the multi-epitope peptide C.A.#4 obtained in Example 6 was examined to determine if the antigenic peptide actually functions as a T cell epitope.

Figure 9:
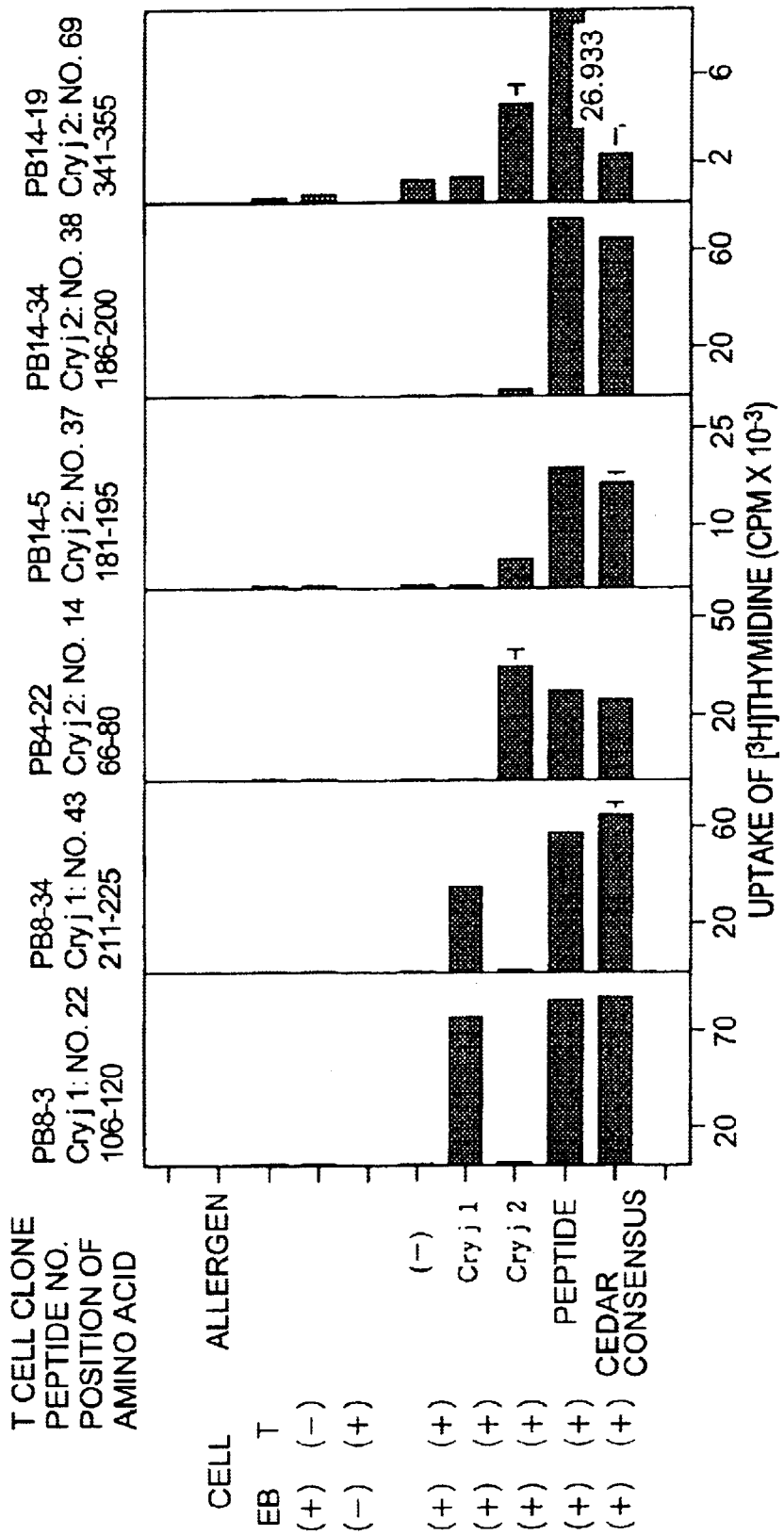
FIG. 9 shows the results of recognizing the T cell epitopes contained in the multi-epitope peptide C.A.#4 by T cell clones.

On a 96-well micro culture plate, a mixture of 5×10⁴ cells of the autologous B cell line previously treated with mitomycin C and 2×10⁴ cells of the T cell clone was incubated for 2 days in 0.2 ml 15% serum-supplemented RPMI-1640 medium, together with, as an antigen, either 50 μg/ml of Cry j 1 and 2 μg/ml of Cry j 2, each antigenic peptide constituting the multi-epitope peptide C.A.#4 or 10 μg/ml C.A.#4 multi-epitope peptide produced by gene expression. After 0.5 μCi [³H] thymidine was added to the medium, incubation was continued for a further 16 hours. After the cells were harvested on a glass filter using a cell harvester, the level of [³H] thymidine taken up into the cells was determined using a liquid scintillation counter. The results are shown in FIG. 9.

T cell clone PB8–3 that recognizes Cry j 1 p106–120, T cell clone PB8-34 that recognizes Cry j 1 p211–225, T cell clone PB4-22 that recognizes Cry j 2 p66–80, T cell clone PB14-5 that recognizes Cry j 2 p181–195, and T cell clone PB14–3 that recognizes Cry j 2 p186–200, all react well with the antigenic peptide. When the multi-epitope peptide was used, the T cell clones are responsive to proliferation at a level comparable to that of each of the peptides. The proliferation response of T cell clone PB14-19 that recognizes Cry j2 p341–355 to the multi-epitope peptide stimulation was somewhat weak.

Those results indicate that the antigenic peptides contained in the multi-epitope peptide function well as the epitopes and retain the T cell activating ability.

EXAMPLE 9

Proliferation Response of the Peripheral Lymphocytes from Patients With Cedar Pollinosis Induced By Multiple-epitope Peptides Since the multi-epitope peptide contains T cell epitope sites, it is necessary to induce proliferation response to peripheral lymphocytes upon applying peptide-based immunotherapy. The inventors thus examined if proliferation response is observed by stimulating peripheral lymphocytes with the multi-epitope peptide.

Peripheral lymphocytes derived from the patients with cedar pollinosis or from healthy subjects were suspended in RPMI-1640 culture medium supplemented with 10% human sera. The suspension was distributed in each well of a 96-well culture plate with a round bottom in a concentration of $2.5 \times 10^5$ cells/200 µl. The multi-epitope peptide represented by SEQ NO: 1, either Cry j 1 or Cry j 2, was added to each well to a final concentration of 0.001 to 20 µg/ml of the multi-epitope peptide, 50 µg/ml of Cry j 1 or 2 µg/ml of Cry j 2. The plate was incubated for 6 days. After 0.5 µCi [$^3$H] thymidine was added to the medium, incubation was continued for a further 16 hours. After the cells were harvested on a glass filter using a cell harvester, the level of [$^3$H] thymidine taken up into the cells was determined using a liquid scintillation counter.

The peripheral lymphocytes from five out of the six patients showed proliferation response to the multi-epitope peptide. The peripheral lymphocytes from one patient and two healthy subjects showed no proliferation scintillation counter.

Figure 10:
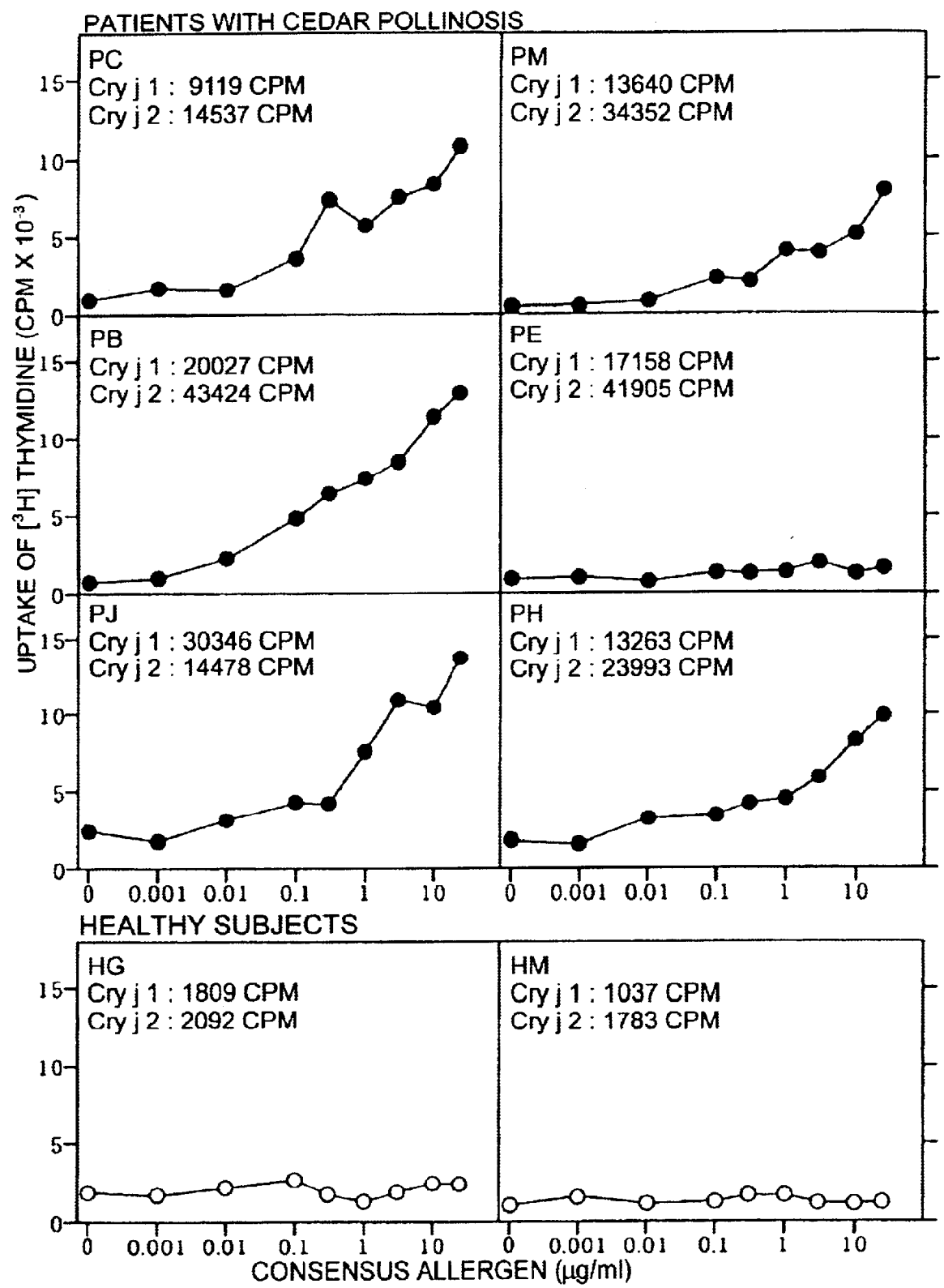
FIG. 10 shows the ability of lymphocyte proliferation response of the peripheral lymphocytes of the patients with cedar pollinosis and healthy subjects induced by stimulation with the multi-epitope peptide (SEQ NO: 1) in various concentrations.

The peripheral lymphocytes from five out of six patients showed proliferation response to the multi-epitope peptide. The peripheral lymphocytes from one patient and two healthy subjects showed no proliferation response (FIG. 10).

Figure 11:
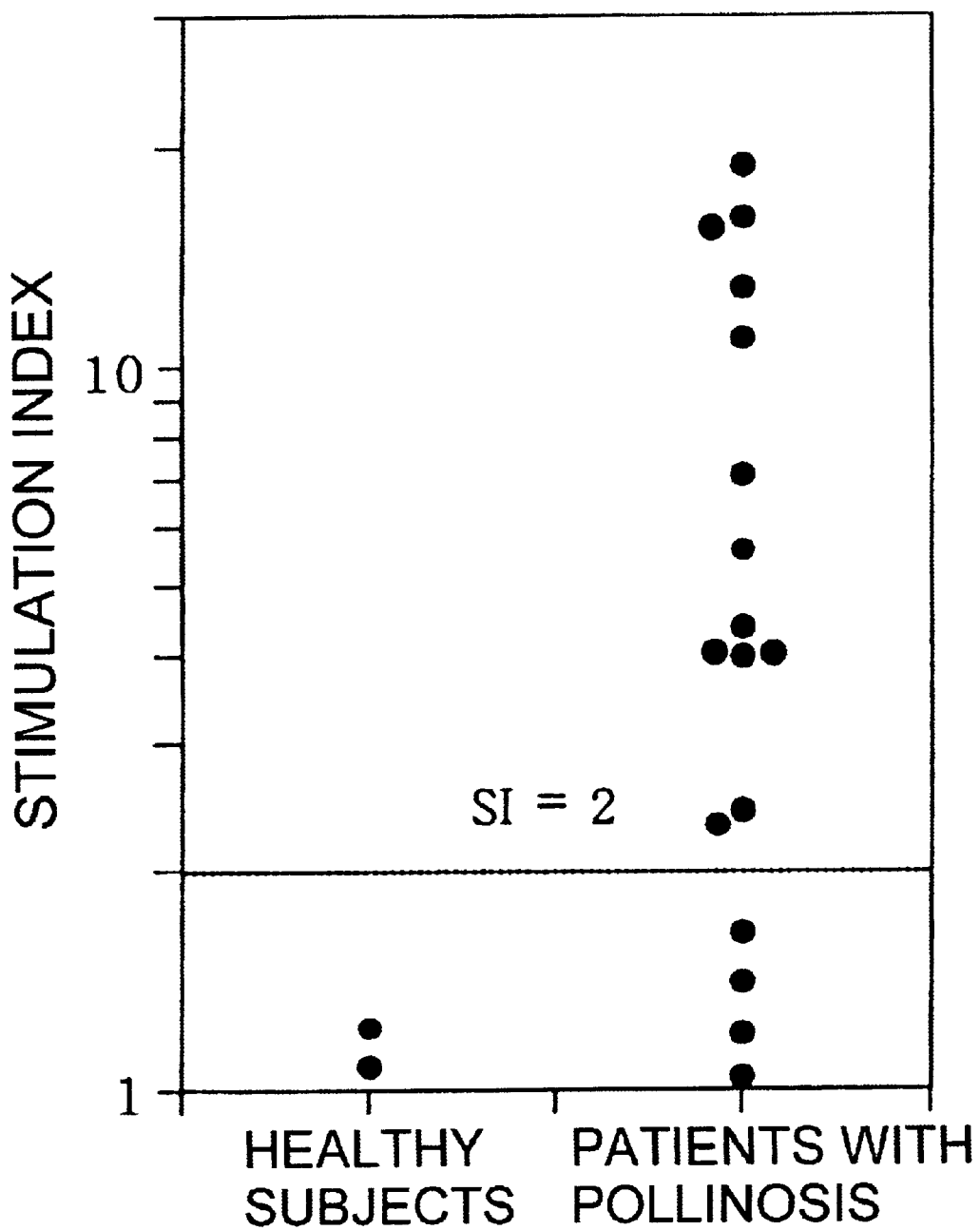
FIG. 11 shows the ability of proliferation response of the peripheral lymphocytes of two healthy subjects and 17 patients with cedar pollinosis induced by stimulation with the multi-epitope peptide SEQ NO: 1.

Peripheral lymphocytes from 17 patients with cedar pollinosis and two healthy subjects were stimulated by 10 µg/ml of the multi-epitope peptide to evaluate T cell response. No response to T cell proliferation was observed with the peripheral lymphocytes from the healthy subjects. In the 17 patients, a maximum [$^3$H] thymidine uptake of 9,652 cpm was observed. When [$^3$H] thymidine uptake of peripheral lymphocytes without antigen stimulation is regarded as 1, the uptake of [$^3$H] thymidine by peripheral lymphocytes in the presence of an antigen is expressed by a stimulation index (SI). The results are shown in FIG. 11. Upon identification of T cell epitopes, SI>2 is regarded to be positive. Similarly, SI>2 is judged to be proliferation responsive to the peptide. Under this criterion, the proliferation response was noted in 13 out of the 17 patients (76.5%). From the results, the peptide-based immunotherapy is effective when administered to 76.5% of the cedar pollinosis patients.

When patients with cedar pollinosis are subjected to the peptide-based immunotherapy using the multi-epitope peptide of the present invention, the proliferation response capability of peripheral lymphocytes from the patients to the multi-epitope peptide can be tested in advance so that the patients responsive to proliferation can be selected. Such a test enables determining if the peptide-based immunotherapy using the multi-epitope peptide is applicable to the individual patient. Therapeutic effects can also be predicted to a certain extent, based on the level of proliferation response.

EXAMPLE 10

Inducing Immune Tolerance by Administering Cedar Pollen Allergen to Mice

Figure 12:
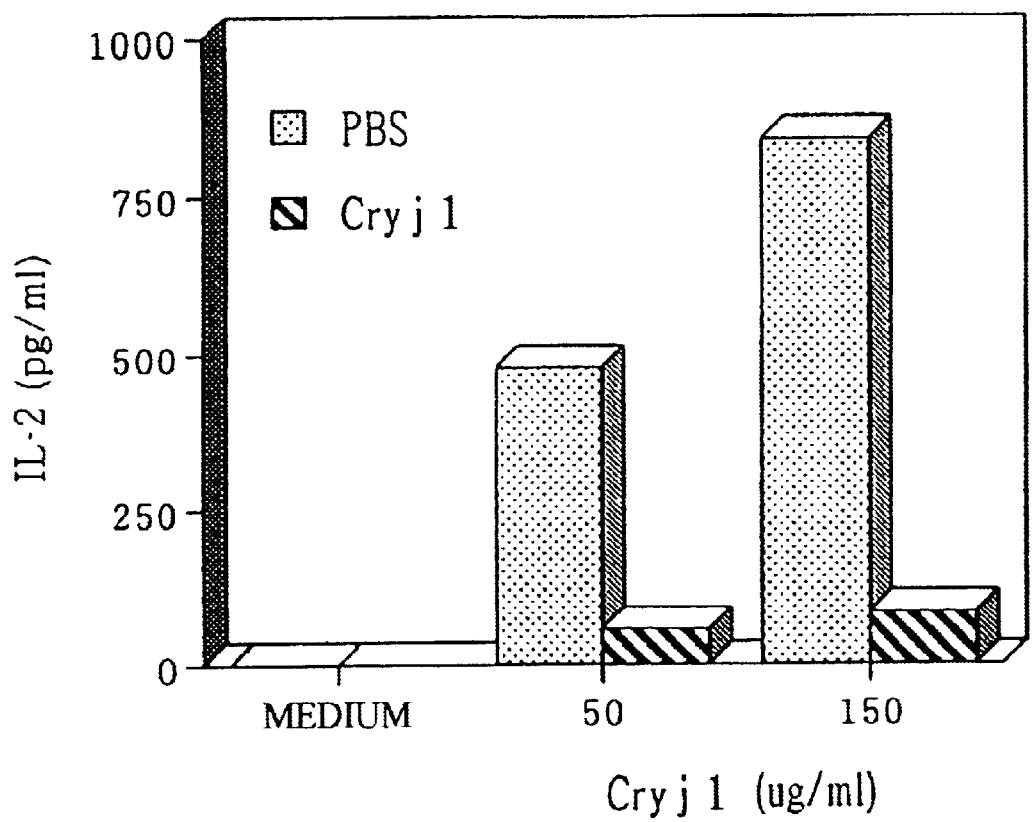
FIG. 12 shows the immune tolerance induced by administration of cedar pollen allergen Cry j 1 to CBF1 mice.

The detailed mechanism in hyposensitization therapy by which cedar pollen allergen is administered for the treatment is yet unknown. To clarify this mechanism, tests were conducted using mice. Cedar pollen allergen Cry j 1 was subcutaneously administered twice to five CBF1 female mice at intervals of 5 days in a dose of 300 µg/mouse. For control, the same dose of PBS was subcutaneously given to five other female mice. Five days later, the animals were sensitized by subcutaneous injection of 100 µg Cry j 1 together with Alum adjuvant. Ten days later, the lymphocytes were isolated to pool them as the lymphocytes from the control group and as the lymphocytes from the Cry j 1-administered mice. Cry j 1 was added to the pooled lymphocytes in doses of 0, 50 and 150 µg/ml. Incubation was performed for 3 days to collect the culture supernatant. IL-2 contained in the supernatant was measured with a device manufactured by Endogen Inc. The results are shown in FIG. 12. In the control (PBS-administered) mouse group, IL-2 production increased as the concentration of Cry j 1 increased from 0 to 50 and 150 µg/ml. In contrast, in the Cry j 1-administered mouse group, IL-2 production was obviously reduced, as compared to the control group, indicating that immune tolerance was acquired by administration of the cedar pollen allergen. The results verify that currently implemented hyposensitization therapy using the cedar pollen allergen is efficacious.

EXAMPLE 11

Identifying T Cell Epitopes in CBF1 Mice

Eight-week-old male CBF1 mice were boosted (i.p.) three times with 10 µg of recombinant Cry j 2 (rCry j 2) at intervals of two weeks together with an adjuvant (Imject Alum, manufactured by Pierce Inc.). One week after the final booster, the spleen cells ($5 \times 10^6$ cells) were cultured together with each of the 74 kinds of Cry j 2 overlapping peptides (0.115 µM) consisting of 15 residues in 0.2 ml RPMI medium (supplemented with 10% FCS, 2 mM L-glutamine, 50 U/ml penicillin and 50 µg/ml streptomycin) in each well of a 96-well plate(manufactured by Falcon Inc.). For control, the reactivities with PBS, 50 µg/ml of Cry j 1, and 0.3 µg/ml of rCry j 2 were also observed. Each reagent was distributed in three wells and incubated at 37° C. for 3 days in 5% $CO_2$. For the last 6 hours, pulse labeling was performed with 0.5 µCi/well of [$^3$H] thymidine. The cells were collected on a glass filter using a cell harvester (Inoteck, Bertold Japan Co., Ltd.). After drying, the level of [$^3$H] thymidine taken up into the cells was determined using a liquid scintillation counter (TRI-CARB 4530, Packard Japan KK).

CBF1 mice immunized with rCry j 2 showed a strong reactivity with its antigen rCry j 2 but did not react with Cry j 1 which is another major cedar pollen allergen. This proved that the reaction is antigen-specific. Among the 74 overlapping peptides tested, CBF1 mice immunized with rCry j 2 showed marked response to Peptide Nos. 14 and 48 as shown in FIG. 2. These results indicate that Peptide Nos. 14 and 48 participate in antigen presentation as the major T cell epitopes in CBF1 mice. Peptides No. 14 and 48 are also known to be major T cell epitope peptides in humans. Therefore, CBF1 mice can be a useful animal model for judging the effectiveness of peptides used for the peptide-based immunotherapy against cedar pollen.

EXAMPLE 12

Immune Response of Antigenic Peptide No. 14 In Vivo

A solution of Peptide No. 14 (3 mg) in physiological saline was subcutaneously injected into each 8-week-old male CBF1 mouse (8 animals/group), twice, once and then again after a 5-day interval. For control, an equal volume (100 µl) of physiological saline was given to the control group in the same manner. On Day 5 after the second administration of the peptide, all mice were sensitized by subcutaneous injection with 50 µg/mouse of rCry j 2, together with Imject Alum. One week after the sensitizaton, the spleen cells were collected from each mouse. The spleen cells ($5 \times 10^6$ cells) were cultured together with 3 µg/ml of rCry j 2 in 0.2 ml RPMI medium (supplemented with 10% FCS, 2 mM L-glutamine, 50 U/ml penicillin and 50 µg/ml streptomycin) in each well of a 96-well plate (manufactured by Falcon Inc.) An incubation was also performed under the same conditions without rCry j 2 for comparison. T cell proliferation was determined in the same manner as in Example 1 using [$^3$H] thymidine. Cytokine was determined using the culture supernatant obtained by stimulating the three peptide-administered groups (0.3, 1.3, and 10 µg/ml) and the control group with 0.3 µg/ml of Cry j 2 in vitro.

Figure 13:
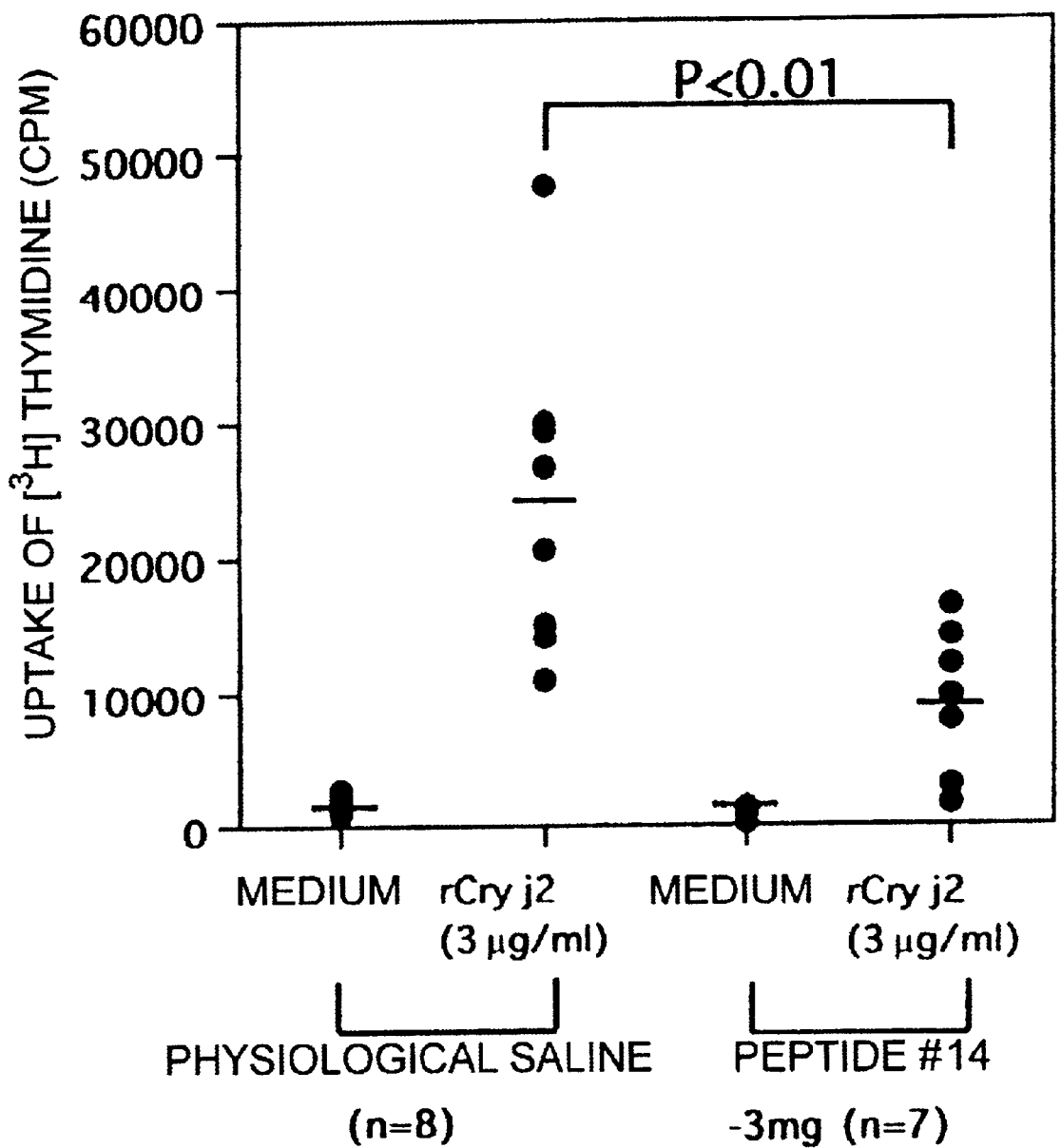
FIG. 13 shows the immune tolerance induced by administration, of Peptide No. 14 (p66–80) of Cry j 2 to CBF1 mice.

When CBF1 mice were previously subcutaneously administered Peptide No. 14, T cell immune response to the subsequent antigen stimulation by rCry j 2 was suppressed significantly ($p<0.01$), as compared to the physiological saline group (FIG. 13). The peptide-administered group showed a significant decrease in IL-2 production as compared to the control group. These results reveal that in the mouse model system, Peptide No. 14 exhibits the preventive effect for cedar pollinosis in the peptide-based immunotherapy.

EXAMPLE 13

Immune Response of Antigenic Peptide No. 48 In Vivo

A solution of Peptide No. 48 (3 mg) in physiological saline was subcutaneously injected into each 6-week-old male CBF1 mouse twice at intervals of 5 days. For control, an equal volume (200 µl) of physiological saline was given in the same manner. There were eight animals each in the peptide-administered group and in the control group. On Day 5 after the second administration of the peptide, all mice were sensitized by subcutaneous injection with 50 µg/mouse of rCry j 2 mixed with an adjuvant (Imject Alum). One week after the sensitization, the spleen cells were collected from each mouse. The spleen cells ($5 \times 10^6$ cells) were cultured together with 3 µg/ml of rCry j 2 in 0.2 ml RPMI medium (supplemented with 10% FCS, 2 mM L-glutamine, 50 U/ml penicillin, and 50 µg/ml streptomycin) in each well of a 96-well plate (manufactured by Falcon Inc.). An incubation was also performed under the same conditions without rCry j 2 for comparison. T cell proliferation was determined in the same manner as in Example 1 using [$^3$H] thymidine.

Figure 14:
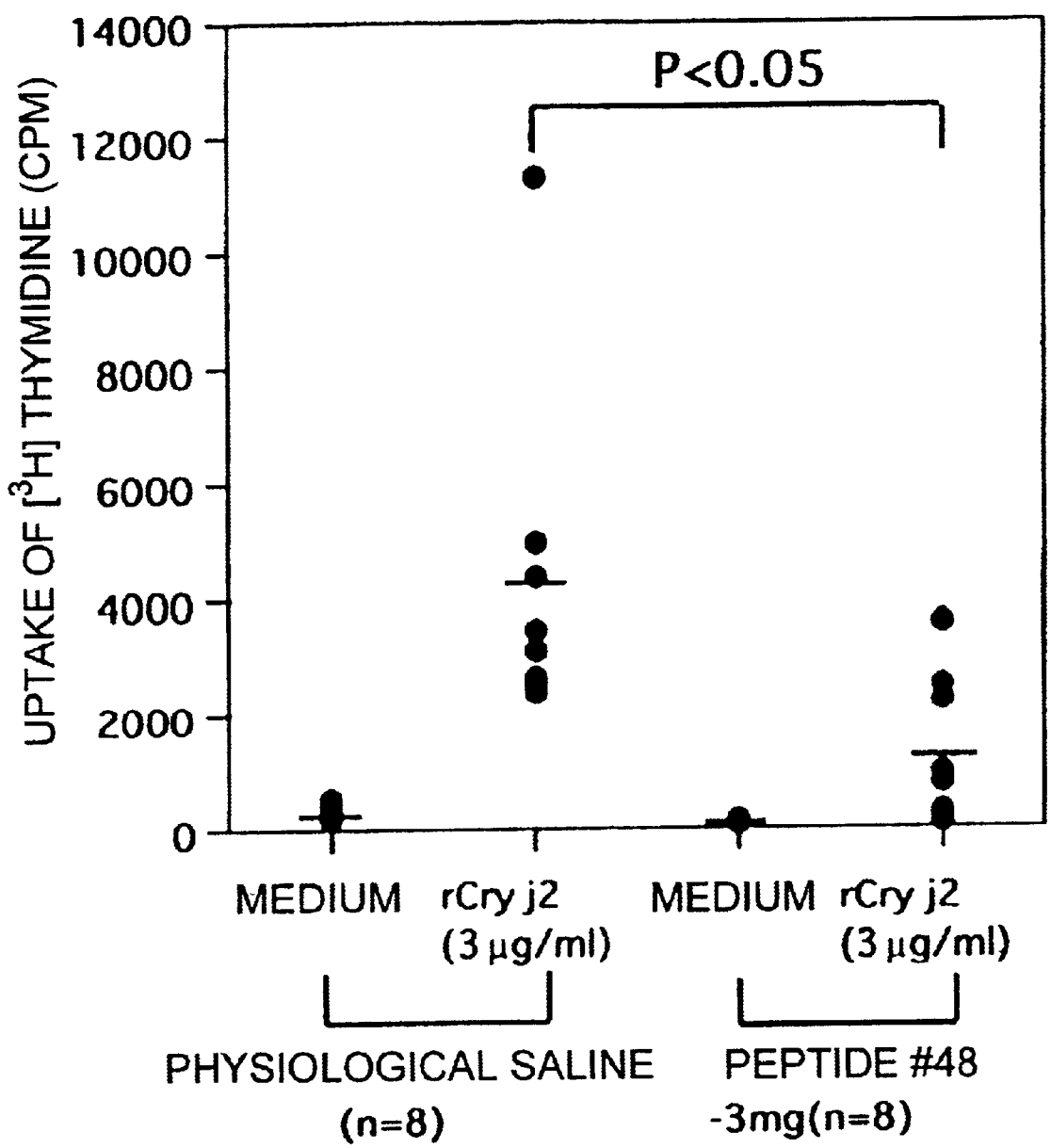
FIG. 14 shows the immune tolerance induced by administration of Peptide No. 48 (p236–250) of Cry j 2 to CBF1 mice.
Figure 17:
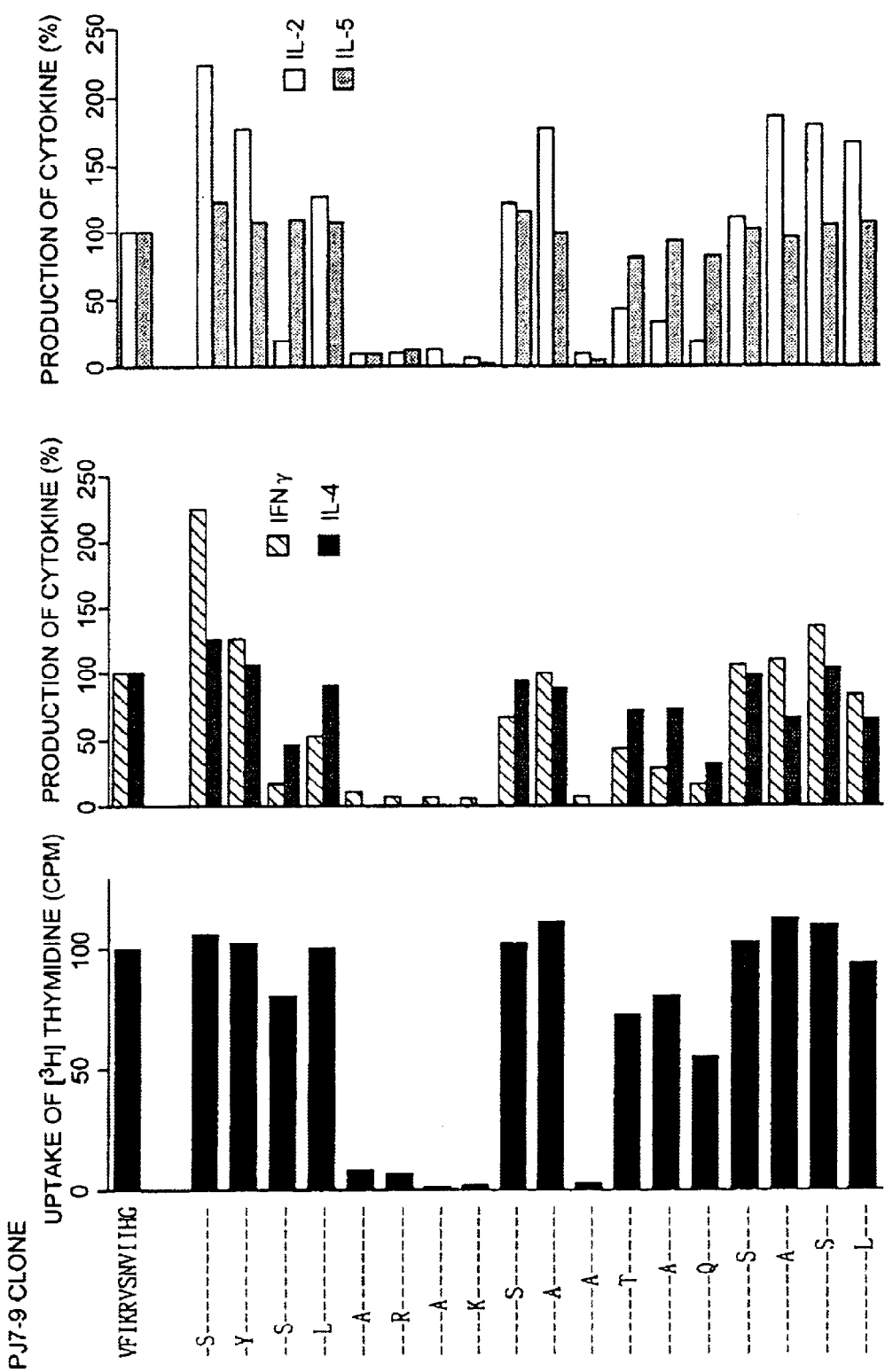
FIG. 17 shows the proliferation response of T cell clone PJ7-9 to an amino acid-substituted analog peptide (SEQ ID NO. 174) of Cry j 1 #22 core peptide and the amount of cytokine subsequently produced.
Figure 18:
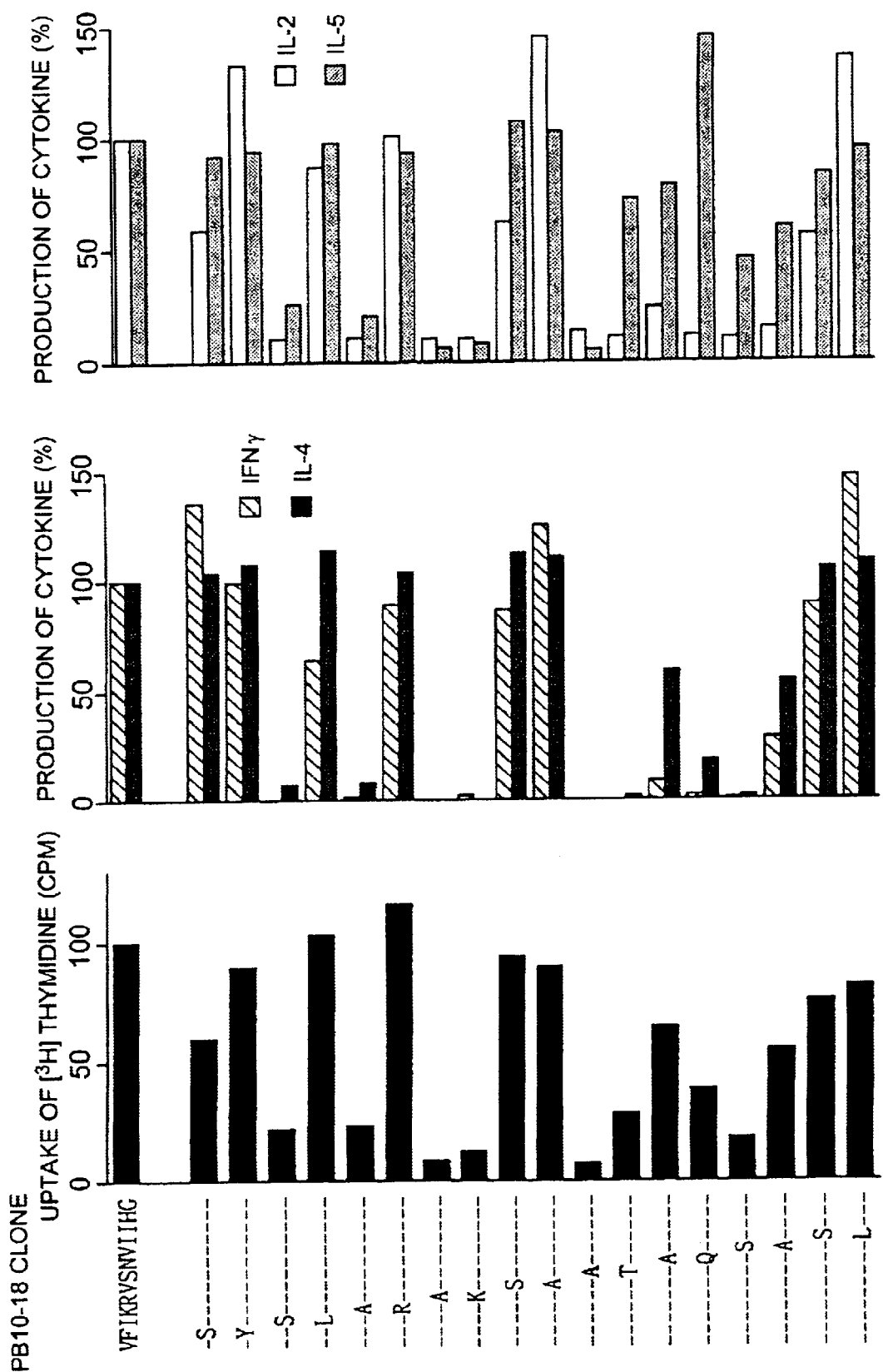
FIG. 18 shows the proliferation response of T cell clone PB10-18 to the above-described analog peptide (SEQ ID NO: 174) and the amount of cytokine subsequently produced.

When CBF1 mice were previously subcutaneously administered Peptide No. 48, T cell immune response to the subsequent antigen stimulation by rCry j 2 was suppressed significantly ($p<0.05$), as compared to the physiological saline-administered group. This result indicates that in the mouse model system, Peptide No. 48 exhibits the preventive effect for cedar pollinosis in peptide-based immunotherapy (FIG. 14).

The experimental results described above reveal that the conventionally implemented hyposensitization therapy in humans using the cedar pollen extract works on the mechanism mediated by the T cell epitope.

EXAMPLE 14

Determination of Core Sequence

To determine the minimum amino acid sequence (core) of the Cry j 1 peptide No. 22 (p106–120) necessary for the T cell line and T cell clone proliferation response, one amino acid residue each was deleted from the N and C terminals of this peptide as shown in FIG. 15 to prepare eleven peptides, i.e., p107–120 (p22-2), P108–120 (p22-3), p109–120 (p22-4), p110–120 (p22-5), p111–120 (p22-6), p106–119 (p22-7), p106–118 (p22-8), p106–117 (p22-9), p106–116 (p22-10), and p106–115 (p22-11) using a peptide synthesizer (PSSM-8, manufactured by Shimadzu Seisakusho Ltd.). The T cell lines (PJ, PR, PB) derived from three patients with cedar pollinosis and which react with Cry j 1 Peptide No. 22, p106–120, and the T cell clones (PB 8-3, PB 8-2, PB 9-39) from one of the patients were examined for the reactivity with these 11 peptides in the same manner as in Examples 1 and 2. Two T cell lines (PJ, PB) and two T cell clones (PB 8-2, PB 9-39) recognized p106–120 (p22-1) and proliferated, but one T cell line and T cell clone did not show any proliferation response (FIG. 15). The results reveal that the p106–120 core sequence consists of nine residues of "FIKRVSNVI"(SEQ ID NO. 7) (the nine residues are designated as Cry j 1 #22 core).

EXAMPLE 15

Multi-eptitone Peptide Containing T Cell Epitopes Derives From Cedar Pollen and Hinoki Pollen Allergens Two peptides (Cha o 1 #8–Cry j 1 #22 core, Cha o 1 #32–Cry j 1 #22 core) were synthesized by joining Peptide No. 8 (p71–90: IFSKNLNIKLNMPLYIAGNK SEQ ID NO. 11) which is a T cell epitope of hinoki pollen allergen Cha o 1 (Japanese Patent Application N. Hei. 8-15327), or Peptide No. 32 (p311–310: SSGKNEGTNIYNNNEAFKVE SEQ ID NO. 12) to Cry j 1 #22 core sequence "FIKRVSNVI"(SEQ ID NO. 7) obtained in Example 14 using a peptide synthesizer (PSSM-8, Shimadzu Seisakusho Ltd.). An RR sequence was inserted between Cha o 1 #8 and Cry j 1 #22 core and between Cha o 1 #32 and Cry j 1 #22 core, that is, Cha o 1 #8–Cry j 1 #22 core (SEQ NO: 4) and Cha o 1 #32–Cry j 1 #22 core (SEQ NO: 5).

A Cry j 1-specific T cell line and a Cha o 1-specific T cell line were prepared from the patients with cedar pollinosis and hinoki pollinosis, respectively. The Cry j 1-specific T cell line and Cha o 1-specific T cell line react with neither the *tubercle bacillus* antigen (PPD) nor the hemolytic streptococcus cell wall (SCW) antigen. The Cry j 1-specific T cell line reacts with Cry j 1 #22 or Cry j 1 #22 core but does not react with Cha o 1 #8 or with Cha o 1 #32. The Cha o 1-specific T cell line reacts with Cha o 1 #8 and #32 but does not react with Cry j 1 #22 or Cry j 1 #22 core (FIG. 16). However, these T cell lines all react with the multi-epitope peptide of SEQ NO: 4 and with the multi-epitope peptide of SEQ NO: 5. These results reveal that the multi-epitope peptides prepared by joining T cell epitopes derived from cedar pollen and hinoki pollen allergens are effective for peptide-based immunotherapy of patients with cedar pollinosis and with hinoki pollinosis.

EXAMPLE 16

The Proliferation Response and the Cytokine Production Which Result From Addition of the Peptides Two clones, PJ7-9 and PB10-18, were employed to see if the activity of T cells can be altered by substituting the amino acids of T cell epitope peptide of the Cry j 1 #22 core. T cell clones PJ 7-9 and PB10-12 which react with Cry j 1 Peptide No. 22 p106–120 are restricted by DRB5*0101 and recognize the nine residues of the Cry j 1 #22 core. Each of the nine amino acids residues in the peptides p108–120 (VFIKRVSNVIIHG SEQ ID NO. 13) of 13 residues including the nine residues were substituted with an homologous amino acid and a non-homologous amino acid to produce analog peptides (FIGS. 17 and 18). The reactivity of T cell clones PJ 7-9 and PB 10-18 with these analog peptides was examined in terms of the uptake of [$^3$H] thymidine. The concentration of cytokine in the reaction solution was measured using a cytokine assay kit manufactured by R & D Systems. The results are shown in FIGS. 17 and 18. The production of IFN-γ, IL-4, IL-2, and IL-5 in the supernatant and the uptake of [$^3$H] thymidine obtained by reacting the peptide of 13 residues with no amino acid substitution were regarded as 100%. In the PJ7-9 clone, the uptake of [$^3$H] thymidine and cytokine production were both markedly suppressed by substituting amino acid Nos. 3, 4 and 6 in Cry j 1 #22 core "FIKRVSNVI(SEQ ID NO. 7)," namely, "K, " "R," and "S," with both homologous and non-homologous amino acids or with only non-homologous amino acids (FIG. 17). Accordingly, the amino acids located in these positions are considered to be important for forming the complex of HLA and T cell receptor molecules via the peptide. Even though the first amino acid (F) is substituted with its homologous amino acid Y, no change is noted in the uptake of [$^3$H] thymidine and production of IL-4 and IL-5, but substitution with a non-homologous amino acid "S" results in a marked increase in IFN-γ and IL-2 production, even though no change is observed in the uptake of [$^3$H] thymidine. For the PB 10-18 clone, the uptake of [3H] thymidine is suppressed by substitution of amino acid No. 1, 2, 3, 4, 6, 7, or 8 of Cry j 1 #22 core. The amino acids located in these positions are considered to be important for forming the complex of HLA and T cell receptor molecules via the peptide. It is further observed that the IL-2 production is suppressed by substitution of amino acid No. 6, 7, or 8, as compared to IL-5 production (FIG. 18). These results reveal that "SIKRVSNVI(SEQ ID NO. 14)" obtained by substituting the first amino acid F with S in Cry j 1 #22 core increases the production of IFN-γ and is thus effective as a therapeutic agent for allergy.

INDUSTRIAL APPLICABILITY

The multi-epitope peptide of the present invention contains T cell epitopes derived from distinct allergen molecules. It contains the peptide presented on the HLA class II molecule encoded by the gene that frequently appears in the population of patients with allergy. It further contains several peptides presented on the HLA class II molecules in different loci (DR, DQ, DP). A peptide-based immunotherapy for effectively treating a wider range of patients could be realized using a multi-epitope peptide of a minimum length.

When patients with allergy are subjected to the peptide-based immunotherapy using the multi-epitope peptide of the present invention, the proliferation response of peripheral lymphocytes from the patients to the peptide can be tested prior to the therapy, to thereby select patients who produce the proliferation response. This test enables judging if the peptide-based immunotherapy with the multi-epitope peptide applies to the patients. The therapeutic effect is also predictable to a certain extent based on the level of the proliferation response.

What is claimed is:

1. A peptide-based immunotherapeutic agent comprising the amino acid sequence of SEQ ID NO: 1.

2. A peptide-based immunotherapeutic agent comprising the amino acid sequence of SEQ ID NO: 2.

3. A peptide-based immnunotherapeutic agent comprising the amino acid sequence of SEQ ID NO: 3.

4. A method of treating cedar pollinosis comprising the administration of a composition comprising a pharmaceutically acceptable carrier or diluent or diluent and a peptide-based immunotherapeutic agent comprising an amino acid sequence selected from the group consisting of SEQ ID NO: 1, 2, and 3.

5. The method according to claim 4, wherein said peptide-based immunotherapeutic agent comprises SEQ ID NO: 1.

6. The method according to claim 4, wherein said peptide-based immunotherapeutic agent comprises SEQ ID NO: 2.

7. The method according to claim 4, wherein said peptide-based immunotherapeutic agent comprises SEQ ID NO: 3.

8. A composition comprising a pharmaceutically acceptable carrier or diluent and a peptide-based immunotherapeutic agent comprising an amino acid sequence selected from the group consisting of SEQ ID NO: 1, 2, and 3.

9. The composition according to claim 8, wherein said peptide-based immunotherapeutic agent comprises SEQ ID NO: 1.

10. The composition according to claim 8, wherein said peptide-based immunotherapeutic agent comprises SEQ ID NO: 2.

11. The composition according to claim 8, wherein said peptide-based immunotherapeutic agent comprises SEQ ID NO: 3.

* * * * *

UNITED STATES PATENT AND TRADEMARK OFFICE
CERTIFICATE OF CORRECTION

| | | |
|---|---|---|
| PATENT NO. | : 6,719,976 B1 | |
| APPLICATION NO. | : 09/142524 | |
| DATED | : April 13, 2004 | |
| INVENTOR(S) | : Toshio Sone et al. | |

It is certified that error appears in the above-identified patent and that said Letters Patent is hereby corrected as shown below:

Title Page:
Item 56, References Cited, Other Publications, Left Column, 4th reference, Taniai *et al*, "Taniai, Madoka, Shunsaku, Ando, Mitsuko Usui, Masashi Kurimoto et al. (Nov. 1988) "N-terminal amino acid sequence of a major allergen of Japanese ceder pollen (Cry J 1)"*60 FEBS LETTERS 239(2):329-332.*"

should read

-- Taniai, Madoka, Shunsaku Ando, Mitsuko Usui, Masashi Kurimoto et al. (Nov. 1988) "N-terminal amino acid sequence of a major allergen of Japanese cedar pollen (*Cry j* 1)" *FEBS LETTERS 239(2):329-332.* --

Title page:
Item 56, References Cited, Other Publications, Right Column, 3rd reference, Matsunaga *et al*, "Matsunaga, Youchi, Toshiji Saibara, Hiroshi Kido, Nobuhiko Katunuma (Jan. 1993) "Participation of cathepsin B in processing of antigen presentation to MHC class II" *FEBS LETTERS 324(3):325-330.*"

should read

--Matsunaga, Youchi, Toshiji Saibara, Hiroshi Kido, Nobuhiko Katunuma (Jan. 1993) "Participation of cathepsin B in processing of antigen presentation to MHC class II" *FEBS LETTERS 324(3):325-330.*--

Title page:
Item 57, Abstract, Line 5 "multi-epitope peptide can treat a wide"

should read

--multi-epitope peptide can prevent and treat a wide--

Column 1:
Line 49 "ßchain"

should read

-- ß-chain --

UNITED STATES PATENT AND TRADEMARK OFFICE
CERTIFICATE OF CORRECTION

PATENT NO.        : 6,719,976 B1
APPLICATION NO. : 09/142524
DATED              : April 13, 2004
INVENTOR(S)      : Toshio Sone et al.

It is certified that error appears in the above-identified patent and that said Letters Patent is hereby corrected as shown below:

Column 3:
Line 8 "77-36"

should read

--77-86--

Column 4:
Line 39 "for each, patient"

should read

--for each patient--

Column 4:
Line 60 "class It molecules"

should read

--class II molecules--

Column 5:
Line 8 "DPB1*10.501"

should read

--DPB1*0501--

Column 7:
Line 62 "(DRB1*140)"

should read

--(DRB1*1405)--

Column 8:
Line 10 "from BCGA antigen."

should read

--from BCGa antigen.--

UNITED STATES PATENT AND TRADEMARK OFFICE
CERTIFICATE OF CORRECTION

PATENT NO.         : 6,719,976 B1
APPLICATION NO. : 09/142524
DATED                  : April 13, 2004
INVENTOR(S)        : Toshio Sone et al.

It is certified that error appears in the above-identified patent and that said Letters Patent is hereby corrected as shown below:

Column 8:
Line 54 "Brief Description of the Sequences" is missing and should read --Brief Description of the Sequences
SEQ ID NOs: 1-174 provide amino acid sequences for various peptides disclosed herein.
SEQ ID NOs: 15 through 174 are found in Figures 1, 2, 7, 15, 17, and 18.--

Column 9:
Line 63 "and Cry j 7"

should read

--and Cry j 2 --

Column 10:
Line 59 "are same"

should read

--are the same--

Column 11:
Line 13 "DQA10102/0301 –"

should read

--DQA1*0102/0301 – --

Column 11:
Line 16 "DPB10501/0402;"

should read

--DPB1*0501/0402;--

UNITED STATES PATENT AND TRADEMARK OFFICE
CERTIFICATE OF CORRECTION

| | |
|---|---|
| PATENT NO. | : 6,719,976 B1 |
| APPLICATION NO. | : 09/142524 |
| DATED | : April 13, 2004 |
| INVENTOR(S) | : Toshio Sone et al. |

It is certified that error appears in the above-identified patent and that said Letters Patent is hereby corrected as shown below:

Column 11:
Line 31 "CD8$^{31}$"

should read

--CD8$^-$ --

Column 12:
Line 14 "Cry j2 p118-195"

should read

--Cry j2 p181-195--

Column 12:
Line 27 "mitomycin C of the"

should read

--mitomycin C or the --

Column 12:
Line 53 "Identifying the Type of T Cell Clone"

should read

--Identifying the Th Type of T Cell Clone--

Column 13:
Line 54 "C.A.#1. a-Arg-Arg-b-Arg-Arg-c-Arg-Arg-e-Arg-Arg"

should read

--C.A.#1. a-Arg-Arg-b-Arg-Arg-c-Arg-Arg-d-Arg-Arg-e --

Column 14:
Line 14 "4-methylumbelliferyl-, ß-D-galacto-pyranoside/0.01 M"

should read

--4-methylumbelliferyl-ß-D-galacto-pyranoside/0.01 M --

UNITED STATES PATENT AND TRADEMARK OFFICE
CERTIFICATE OF CORRECTION

| | |
|---|---|
| PATENT NO. | : 6,719,976 B1 |
| APPLICATION NO. | : 09/142524 |
| DATED | : April 13, 2004 |
| INVENTOR(S) | : Toshio Sone et al. |

It is certified that error appears in the above-identified patent and that said Letters Patent is hereby corrected as shown below:

Column 14:
Line 16 "NaN, and"

should read

--$NaN_3$ and--

Column 15:
Lines 38-39 "proliferation scintillation counter."

should read

--proliferation response (Fig. 10).--

Column 15:
Lines 40-43 "This paragraph is the same as the preceding paragraph."

should read

--This paragraph should not be repeated.--

Column 15:
Lines 40-43 "The peripheral lymphocytes from five out of six patients showed proliferation response to the multi-epitope peptide. The peripheral lymphocytes from one patient and two healthy subjects showed no proliferation response (FIG. 10)."

should read

--The proliferation response of peripheral lymphocytes began to occur with stimulation of 01.μg/ml of the multi-epitope peptide and increased dose-dependently. Based on the results, the concentration of the multi-epitope peptide required for inducing T cell proliferation response in vitro is at least 10μg/ml.--

Column 16:
Line 45 "spleen cells ($5 \times 10^6$ cells) were cultured"

should read

--spleen cells were collected from three mice and mixed together. The spleen cells

UNITED STATES PATENT AND TRADEMARK OFFICE
CERTIFICATE OF CORRECTION

PATENT NO.       : 6,719,976 B1                                    Page 6 of 6
APPLICATION NO.  : 09/142524
DATED            : April 13, 2004
INVENTOR(S)      : Toshio Sone et al.

It is certified that error appears in the above-identified patent and that said Letters Patent is hereby corrected as shown below:

($5 \times 10^6$ cells)--

Column 18:
Line 48 "N. Hei 8-15327), or "

should read

--No. Hei 8-153527), or--

Column 20:
Line 30, Claim 3 "A peptide-based immnunotherapeutic"

should read

-- A peptide-based immunotherapeutic --

Column 20:
Line 34, Claim 4 "carrier or diluent or diluent and"

should read

--carrier or diluent and--

Signed and Sealed this

Eighteenth Day of September, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,719,976 B1 |
| APPLICATION NO. | : 09/142524 |
| DATED | : April 13, 2004 |
| INVENTOR(S) | : Toshio Sone et al. |

It is certified that error appears in the above-identified patent and that said Letters Patent is hereby corrected as shown below:

Title Page:
Item 56, References Cited, Other Publications, Left Column, 4th reference, Taniai *et al*, "Taniai, Madoka, Shunsaku, Ando, Mitsuko Usui, Masashi Kurimoto et al. (Nov. 1988) "N-terminal amino acid sequence of a major allergen of Japanese ceder pollen (Cry J 1)"*60 FEBS LETTERS 239(2):329-332*."

should read

-- Taniai, Madoka, Shunsaku Ando, Mitsuko Usui, Masashi Kurimoto et al. (Nov. 1988) "N-terminal amino acid sequence of a major allergen of Japanese cedar pollen (*Cry j* 1)" *FEBS LETTERS 239(2):329-332*. --

Title page:
Item 56, References Cited, Other Publications, Right Column, 3rd reference, Matsunaga *et al*, "Matsunaga, Youchi, Toshiji Saibara, Hiroshi Kido, Nobuhiko Katunuma (Jan. 1993) "Participation of cathepsin B in processing of antigen presentation to MHC class II" *FEBS LETTERS 324(3):325-330*."

should read

--Matsunaga, Youchi, Toshiji Saibara, Hiroshi Kido, Nobuhiko Katunuma (Jan. 1993) "Participation of cathepsin B in processing of antigen presentation to MHC class II" *FEBS LETTERS 324(3):325-330*.--

Title page:
Item 57, Abstract, Line 5 "multi-epitope peptide can treat a wide"

should read

--multi-epitope peptide can prevent and treat a wide--

Column 1:
Line 49 "ßchain"

should read

-- ß-chain --

UNITED STATES PATENT AND TRADEMARK OFFICE
CERTIFICATE OF CORRECTION

PATENT NO. : 6,719,976 B1
APPLICATION NO. : 09/142524
DATED : April 13, 2004
INVENTOR(S) : Toshio Sone et al.

It is certified that error appears in the above-identified patent and that said Letters Patent is hereby corrected as shown below:

Column 3:
Line 8 "77-36"

should read

--77-86--

Column 4:
Line 39 "for each, patient"

should read

--for each patient--

Column 4:
Line 60 "class It molecules"

should read

--class II molecules--

Column 5:
Line 8 "DPB1*10.501"

should read

--DPB1*0501--

Column 7:
Line 62 "(DRB1*140)"

should read

--(DRB1*1405)--

Column 8:
Line 10 "from BCGA antigen."

should read

--from BCGa antigen.--

UNITED STATES PATENT AND TRADEMARK OFFICE
CERTIFICATE OF CORRECTION

PATENT NO. : 6,719,976 B1
APPLICATION NO. : 09/142524
DATED : April 13, 2004
INVENTOR(S) : Toshio Sone et al.

It is certified that error appears in the above-identified patent and that said Letters Patent is hereby corrected as shown below:

Column 8:
Line 54 "Brief Description of the Sequences" is missing and should read --Brief Description of the Sequences
SEQ ID NOs: 1-174 provide amino acid sequences for various peptides disclosed herein.
SEQ ID NOs: 15 through 174 are found in Figures 1, 2, 7, 15, 17, and 18.--

Column 9:
Line 63 "and Cry j 7"

should read

--and Cry j 2 --

Column 10:
Line 59 "are same"

should read

--are the same--

Column 11:
Line 13 "DQA10102/0301 –"

should read

--DQA1*0102/0301 – --

Column 11:
Line 16 "DPB10501/0402;"

should read

--DPB1*0501/0402;--

UNITED STATES PATENT AND TRADEMARK OFFICE
CERTIFICATE OF CORRECTION

PATENT NO. : 6,719,976 B1
APPLICATION NO. : 09/142524
DATED : April 13, 2004
INVENTOR(S) : Toshio Sone et al.

It is certified that error appears in the above-identified patent and that said Letters Patent is hereby corrected as shown below:

Column 11:
Line 31 "$CD8^{31}$"

should read

--$CD8^-$--

Column 12:
Line 14 "Cry j2 p118-195"

should read

--Cry j2 p181-195--

Column 12:
Line 27 "mitomycin C of the"

should read

--mitomycin C or the --

Column 12:
Line 53 "Identifying the Type of T Cell Clone"

should read

--Identifying the Th Type of T Cell Clone--

Column 13:
Line 54 "C.A.#1. a-Arg-Arg-b-Arg-Arg-c-Arg-Arg-e-Arg-Arg"

should read

--C.A.#1. a-Arg-Arg-b-Arg-Arg-c-Arg-Arg-d-Arg-Arg-e --

Column 14:
Line 14 "4-methylumbelliferyl-, ß-D-galacto-pyranoside/0.01 M"

should read

--4-methylumbelliferyl-ß-D-galacto-pyranoside/0.01 M --

UNITED STATES PATENT AND TRADEMARK OFFICE
CERTIFICATE OF CORRECTION

| | |
|---|---|
| PATENT NO. | : 6,719,976 B1 |
| APPLICATION NO. | : 09/142524 |
| DATED | : April 13, 2004 |
| INVENTOR(S) | : Toshio Sone et al. |

It is certified that error appears in the above-identified patent and that said Letters Patent is hereby corrected as shown below:

Column 14:
Line 16 "NaN, and"

should read

--$NaN_3$ and--

Column 15:
Lines 38-39 "proliferation scintillation counter."

should read

--proliferation response (Fig. 10).--

Column 15:
Lines 40-43 "This paragraph is the same as the preceding paragraph."

should read

--This paragraph should not be repeated.--

Column 15:
Lines 40-43 "The peripheral lymphocytes from five out of six patients showed proliferation response to the multi-epitope peptide. The peripheral lymphocytes from one patient and two healthy subjects showed no proliferation response (FIG. 10)."

should read

--The proliferation response of peripheral lymphocytes began to occur with stimulation of 0.1μg/ml of the multi-epitope peptide and increased dose-dependently. Based on the results, the concentration of the multi-epitope peptide required for inducing T cell proliferation response in vitro is at least 10μg/ml.--

Column 16:
Line 45 "spleen cells ($5 \times 10^6$ cells) were cultured"

should read

--spleen cells were collected from three mice and mixed together. The spleen cells

UNITED STATES PATENT AND TRADEMARK OFFICE
CERTIFICATE OF CORRECTION

| | |
|---|---|
| PATENT NO. | : 6,719,976 B1 |
| APPLICATION NO. | : 09/142524 |
| DATED | : April 13, 2004 |
| INVENTOR(S) | : Toshio Sone et al. |

It is certified that error appears in the above-identified patent and that said Letters Patent is hereby corrected as shown below:

($5 \times 10^6$ cells)--

Column 18:
Line 48 "N. Hei 8-15327), or "

should read

--No. Hei 8-153527), or--

Column 20:
Line 30, Claim 3 "A peptide-based immnunotherapeutic"

should read

-- A peptide-based immunotherapeutic --

Column 20:
Line 34, Claim 4 "carrier or diluent or diluent and"

should read

--carrier or diluent and--

This certificate supersedes the Certificate of Correction issued September 18, 2007.

Signed and Sealed this

Ninth Day of December, 2008

JON W. DUDAS
*Director of the United States Patent and Trademark Office*